(12) United States Patent
Tillotson et al.

(10) Patent No.: US 9,358,212 B2
(45) Date of Patent: Jun. 7, 2016

(54) HIGHLY COMPACTABLE AND DURABLE DIRECT COMPRESSION EXCIPIENTS AND EXCIPIENT SYSTEMS

(71) Applicant: SPI Pharma, Inc., Wilmington, DE (US)

(72) Inventors: John Tillotson, Hudsonville, MI (US); Cecil Propst, Norton Shores, MI (US)

(73) Assignee: SPI Pharma, Inc., Wilmington, DE (US)

( * ) Notice: Subject to any disclaimer, the term of this patent is extended or adjusted under 35 U.S.C. 154(b) by 0 days.

(21) Appl. No.: 14/097,773

(22) Filed: Dec. 5, 2013

(65) Prior Publication Data

US 2014/0093574 A1 Apr. 3, 2014

Related U.S. Application Data

(63) Continuation of application No. 12/661,016, filed on Mar. 9, 2010, now Pat. No. 8,617,588.

(60) Provisional application No. 61/158,566, filed on Mar. 9, 2009.

(51) Int. Cl.
*A61K 9/00* (2006.01)
*A61K 31/167* (2006.01)
*A61K 47/26* (2006.01)
*A61K 9/20* (2006.01)

(52) U.S. Cl.
CPC ............ *A61K 9/2018* (2013.01); *A61K 9/0056* (2013.01); *A61K 31/167* (2013.01); *A61K 47/26* (2013.01)

(58) Field of Classification Search
CPC .... A61K 47/26; A61K 9/2018; A61K 9/0056
See application file for complete search history.

(56) References Cited

U.S. PATENT DOCUMENTS

| 4,605,794 A | 8/1986 | Reiff et al. |
|---|---|---|
| 4,832,956 A | 5/1989 | Gergely et al. |
| 4,990,537 A | 2/1991 | Okuyama et al. |
| 5,382,434 A | 1/1995 | de Haan et al. |
| 5,464,632 A | 11/1995 | Cousin et al. |

(Continued)

FOREIGN PATENT DOCUMENTS

| EP | 1161940 | 12/2001 |
|---|---|---|
| WO | 99/58704 | 11/1999 |
| WO | 03/051338 | 6/2003 |

OTHER PUBLICATIONS

Merck Index, 14th Edition, Maryadele O'Neil, ed. (2006), entries for mannitol, glucose, sucrose, and starch.

*Primary Examiner* — Robert A Wax
*Assistant Examiner* — Thor Nielsen
(74) *Attorney, Agent, or Firm* — Morgan, Lewis & Bockius LLP

(57) ABSTRACT

The present invention relates to solid dispersions including, but not limited to, co-processed carbohydrates with different solubilities and concentrations, which have a microcrystalline plate structure. The solid dispersions, excipient systems and formulations of the present invention are highly compactable and durable and when compressed into solid dosage forms demonstrate uniform densification, low friability at low pressures, and and/or relatively constant low disintegration times at various hardnesses. The solid dosage forms of the present invention demonstrate superior organoleptics, disintegration, and/or robustness.

20 Claims, 28 Drawing Sheets

(56) References Cited

U.S. PATENT DOCUMENTS

| | | |
|---|---|---|
| 5,489,439 A * | 2/1996 | Bola .................... 424/489 |
| 5,576,014 A | 11/1996 | Mizumoto et al. |
| 5,583,215 A | 12/1996 | Kawashima et al. |
| 5,635,210 A | 6/1997 | Allen, Jr. et al. |
| 5,720,974 A | 2/1998 | Makino et al. |
| 5,958,453 A | 9/1999 | Ohno et al. |
| 5,958,471 A | 9/1999 | Schwarz et al. |
| 6,024,981 A | 2/2000 | Khankari et al. |
| 6,106,861 A | 8/2000 | Chauveau et al. |
| 6,114,369 A | 9/2000 | Tanikawa et al. |
| 6,149,941 A | 11/2000 | Schwarz et al. |
| 6,165,511 A | 12/2000 | Schwarz et al. |
| 6,221,392 B1 | 4/2001 | Khankari et al. |
| 6,248,359 B1 | 6/2001 | Faour |
| 6,274,727 B1 | 8/2001 | Maul et al. |
| 6,284,270 B1 | 9/2001 | Lagoviyer et al. |
| 6,669,957 B1 | 12/2003 | Laruelle et al. |
| 6,740,339 B1 | 5/2004 | Ohkouchi et al. |
| 6,814,978 B2 | 11/2004 | Bunick et al. |
| 6,845,571 B1 | 1/2005 | Schwarz et al. |
| 6,861,069 B2 | 3/2005 | Schwarz et al. |
| 6,872,405 B2 | 3/2005 | Takaishi et al. |
| 7,118,765 B2 | 10/2006 | Norman et al. |
| 7,282,217 B1 | 10/2007 | Grimshaw et al. |
| 8,545,889 B2 | 10/2013 | Norman et al. |
| 2002/0002172 A1 | 1/2002 | Bell-Huff et al. |
| 2002/0071864 A1 | 6/2002 | Kim et al. |
| 2003/0118642 A1 | 6/2003 | Norman et al. |
| 2003/0188679 A1 | 10/2003 | Schwarz et al. |
| 2004/0071772 A1 | 4/2004 | Narita et al. |
| 2004/0121006 A1 | 6/2004 | Narita et al. |
| 2005/0019391 A1 | 1/2005 | Gendrot et al. |
| 2005/0106240 A1 | 5/2005 | Tanaka et al. |
| 2006/0251716 A1 | 11/2006 | Norman et al. |
| 2007/0092562 A1 | 4/2007 | Norman et al. |
| 2007/0275058 A1 | 11/2007 | Tanaka et al. |
| 2008/0241237 A1 | 10/2008 | Venkatesh |
| 2008/0299194 A1 | 12/2008 | Kolter et al. |
| 2010/0226964 A1 | 9/2010 | Tillotson et al. |

* cited by examiner

HIGHLY COMPACTABLE AND DURABLE DIRECT COMPRESSION EXCIPIENTS AND EXCIPIENT SYSTEMS

CROSS-REFERENCE TO RELATED APPLICATIONS

This application is a continuation of U.S. patent application Ser. No. 12/661,016, filed Mar. 9, 2010, now U.S. Pat. No. 8,617,588, which claims priority to U.S. Provisional Patent Application No. 61/158,566, filed Mar. 9, 2009, each of which is hereby incorporated by reference in its entirety.

FIELD OF THE INVENTION

The present invention relates to a highly compactable and durable solid dispersion, and excipient system made therefrom, comprising co-processed carbohydrates which have different solubilities and/or concentrations, and microcrystalline plate structure, and formulations produced therefrom, which formulations are directly compressible into solid dosage forms. In some embodiments of the present invention the solid dosage forms demonstrate superior organoleptics, fast disintegration, and/or good robustness. In some embodiments the present invention also includes, but is not limited to, the solid dosage forms produced by directly compressing the co-processed solid dispersion and/or excipient system.

In some embodiments, the present invention also relates to solid dispersions of co-processed carbohydrates that produce formulations that are directly compressible into solid dosage forms, which solid dispersions have a microcrystalline plate structure.

BACKGROUND OF THE INVENTION

Existing excipients and excipient systems, such as commercially available directly compressible mannitol products require higher pressures to achieve a packagable tablet. As a result, there can be a loss in disintegration time caused by loss of porosity at similar hardness. Insoluble filler-binders, such as microcrystalline cellulose, can be used to make acceptable tablets at lower pressures but may lead to poor stability and/or dissolution and have poor mouth feel. Higher pressures may lead to the rupturing of many coated active pharmaceutical ingredients (APIs). High percentage sorbitol (>6%) products are more acceptable from a pressure profile but may lead to poor stability and require higher levels of disintegrants to reach a less than 60 second disintegration time. The higher pressure needed for tablet durability restricts the coating type, coating formulation and thickness of coating that can be used on the API in oral dispersible tablets. This restriction requires excipients and coatings that survive better during the compaction process. Many sparingly soluble APIs are micronized. It is important to maintain surface area for these APIs to obtain the desired dissolution profile. Higher pressure can cause agglomeration of micronized APIs in the compression step and the merging of API particles and loss of surface area. Some APIs such as aspirin are very soft and deformable, and during compression pressure relocate these soft APIs to the tablet surface especially in smaller sized tablets. It is important to use low pressure excipients that are water soluble that can also flow readily with the API with compression pressure in order to maintain the disintegration and subsequent dissolution time of the tablet and prevent tablet surfaces from becoming hydrophobic by the API movement.

BRIEF SUMMARY OF THE INVENTION

One embodiment of the present invention relates to a highly compactable solid dispersion and excipient system including, but not limited to, co-processed carbohydrates which have different solubilities and which form a layered microcrystalline plate structure, and formulations produced therefrom. In one embodiment, such formulations are directly compressible into solid dosage forms, some of which demonstrate superior organoleptics, disintegration, and/or robustness. In one embodiment, the invention also includes, but is not limited to, solid dosage forms produced by directly compressing the co-processed solid dispersion excipient system. In one embodiment, the present invention also relates to solid dispersions of co-processed carbohydrates that produce formulations that are directly compressible into solid dosage forms.

In one embodiment, the microcrystalline plate structure of the solid dispersion of the present invention allows for the production of solid dosage forms having uniform densification, low friability at low pressures, and/or relatively constant low disintegration times at various hardnesses.

According to some embodiments of the invention, a solid dispersion includes a mixture of at least two carbohydrates, wherein a first carbohydrate is present in an amount of about 70 wt % to about 99.5 wt % and a second carbohydrate is present in an amount of about 0.5 wt % to about 30 wt %. In some embodiments, the first and/or second carbohydrates include polyols. In certain embodiments, the at least two carbohydrates are co-spray dried. In some embodiments, a solid dispersion including a mixture of at least two carbohydrates is included in a pharmaceutical formulation.

In some embodiments, the carbohydrates include mannitol, maltitol, isomalt and/or sorbitol. In some embodiments, the first carbohydrate includes mannitol and the second carbohydrate includes maltitol. In certain embodiments, mannitol and maltitol are present in a ratio of about 88:12 to about 99.5:0.5. In some embodiments, an excipient system includes a solid dispersion and a disintegrant, such as crospovidone.

According to some embodiments, a solid dispersion includes at least three carbohydrates, wherein a first carbohydrate is present in an amount of about 70 wt % to about 99.5 wt %, a second carbohydrate is present in an amount of about 0.5 wt % to about 30 wt %, and a third carbohydrate is present an amount of about 0.5 wt % to about 30 wt %. In some embodiments, the first, second, and/or third carbohydrates include polyols. In some embodiments, the at least three carbohydrates are co-spray dried. In some embodiments the at least three carbohydrates are fluid bed granulated. In some embodiments, the at least three carbohydrates are co-granulated. In some embodiments, the at least three carbohydrates include mannitol, maltitol, lactitol, glucose, isomalt, and/or sorbitol. In certain embodiments, the first carbohydrate includes mannitol, the second carbohydrate includes maltitol, and the third carbohydrate includes sorbitol. In some embodiments, a pharmaceutical formulation includes a solid dispersion with a mixture of at least three carbohydrates. In certain embodiments, an excipient system includes a solid dispersion and a disintegrant, such as crospovidone.

According to some embodiments, a solid dispersion includes a coated carbohydrate or carbohydrate mixture. In some embodiments, a coated carbohydrate includes a coated polyol and/or a coated sugar. In some embodiments, a coated carbohydrate mixture includes a coated polyol mixture and/or a coated sugar mixture. In some embodiments, an excipient system includes a coated polyol mixture. In certain embodiments, a coated polyol includes mannitol, such as spray dried mannitol. In some embodiments, a coated carbohydrate or coated carbohydrate mixture has a coating including, but not limited to a 60:40 copolymer of vinylpyrrolidone and vinyl acetate. In some embodiments, an excipient system includes a solid dispersion and a disintegrant, such as crospovidone. In some embodiments, a pharmaceutical formulation includes an excipient system with a coated carbohydrate or carbohydrate mixture.

According to some embodiments, a solid dispersion includes a mixture of at least two carbohydrates, and a coated carbohydrate or carbohydrate mixture. In some embodiments, the carbohydrates include polyols. In some embodiments, the at least two carbohydrates are co-spray dried. In certain embodiments, the at least two carbohydrates are fluid bed granulated. In certain embodiments, the at least two carbohydrates are co-granulated. In some embodiments, the at least two carbohydrates include mannitol, isomalt, maltitol, lactitol and/or sorbitol. In some embodiments, the at least two carbohydrates include about 70 wt % to about 99.5 wt % mannitol and about 0.5 wt % to about 30 wt % maltitol. In some embodiments, the coated carbohydrate includes a coated polyol and/or a coated sugar. In some embodiments, the coated carbohydrate mixture includes a coated sugar mixture and/or a coated polyol mixture. In certain embodiments, the coated carbohydrate has a coating including, but not limited to a 60:40 copolymer of vinylpyrrolidone and vinyl acetate. In some embodiments, an excipient system including a mixture of at least two carbohydrates, and a coated carbohydrate or carbohydrate mixture further includes an active, a polyol, such as spray dried mannitol, and/or a disintegrant such as crospovidone. In some embodiments, a pharmaceutical formulation includes an excipient system including a mixture of at least two carbohydrates, and coated carbohydrate or carbohydrate mixture. In some embodiments, a pharmaceutical formulation includes about 25 wt % to about 99 wt % of an excipient system.

According to some embodiments, an excipient system includes, but is not limited to a mixture of at least three carbohydrates and a coated polyol or coated polyol mixture. In some embodiments, the at least three carbohydrates include polyols. In some embodiments, the mixture of at least three carbohydrates is co-spray dried or co-granulated. In certain embodiments, the mixture of at least three carbohydrates includes mannitol, maltitol, isomalt, and/or sorbitol. In certain embodiments, the at least three carbohydrates include about 70 wt % to about 99.5 wt % mannitol about 0.5 wt % to about 30 wt % maltitol, and about 0.5 wt % to about 30 wt % sorbitol. In some embodiments, the coated polyol has a coating including, but not limited to a 60:40 copolymer of vinylpyrrolidone and vinyl acetate. In some embodiments, an excipient system including a solid dispersion of at least three carbohydrates and a coated polyol or coated polyol mixture, further includes an active, a polyol such as spray dried mannitol and/or a disintegrant such as crospovidone.

In some embodiments, a pharmaceutical formulation includes an excipient system including a solid dispersion of at least three carbohydrates, and a coated carbohydrate or carbohydrate mixture. In some embodiments, a pharmaceutical formulation further includes an active and/or a disintegrant such as crospovidone. In some embodiments, a pharmaceutical formulation further includes about 25 wt % to about 99 wt % of an excipient system.

BRIEF DESCRIPTION OF THE DRAWINGS

The foregoing summary, as well as the following detailed description of the invention will be better understood when read in conjunction with the appended drawings. For the purpose of illustrating the invention, there are shown in the drawings preferred embodiment(s). It should be understood, however, that the invention is not limited to the precise arrangements and instrumentalities shown. In the drawings:

FIG. 6, comprising FIGS. 6A-6K, is a set of SEMs of different mannitol compositions after they are dried in spray dryer.

FIG. 6A is a SEM (magnification 100×) of spray dried mannitol Mannogem® EZ EP grade produced by SPI Pharma, Inc.

FIG. 6B represents FIG. 6A at 1000× magnification.

FIG. 6C represents FIG. 6A at 2000× magnification.

FIG. 6D is a SEM (magnification 100×) of spray dried mannitol Mannogem®-EZ USP grade produced by SPI Pharma, Inc.

FIG. 6E represents FIG. 6D at 1000× magnification.

FIG. 6F represents FIG. 6D at 2000× magnification.

FIG. 6G is a SEM (magnification 100×) of spray dried mannitol HS produced by SPI Pharma, Inc.

FIG. 6H represents FIG. 6G at 1000× magnification.

FIG. 6I represents FIG. 6G at 2000× magnification.

FIG. 6J is a SEM (magnification 1000×) of spray dried mannitol Parteck® M 200 EP grade produced by Merck KGaA.

FIG. 6K represents FIG. 6J at 2000× magnification.

FIG. 7, comprising

FIG. 7A is a SEM (magnification 100×) of Solid Dispersion A.

FIG. 7B represents FIG. 7A at 1000× magnification.

FIG. 7C represents FIG. 7A at 2000× magnification.

DETAILED DESCRIPTION OF THE INVENTION

Figure 1:
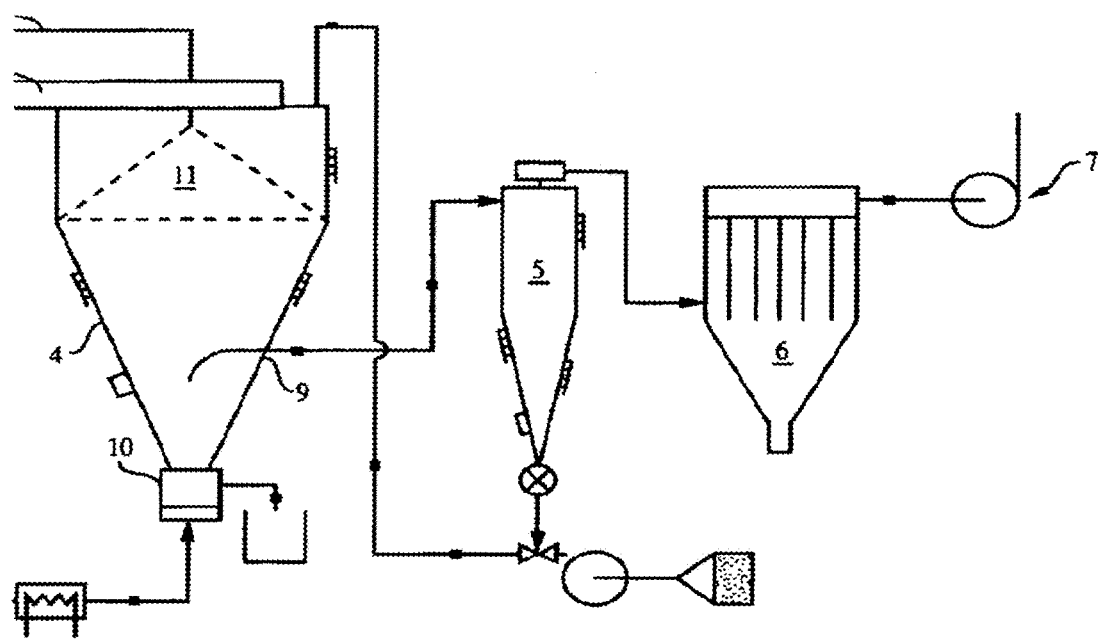
FIG. 1 is a flow diagram depicting a process for co-sprayed fluid-bed spray drying.

The following detailed description is exemplary and explanatory and is intended to provide further explanation of the invention described herein. Other advantages, and novel features will be readily apparent to those skilled in the art from the following detailed description of the invention.

In one embodiment, the aim of the present invention was to overcome the drawbacks of existing excipients and excipient systems and provide excipient systems that increase compactability and tablet durability at lower compression forces, improve tablet hardness, stability, decrease disintegration time and/or improve organoleptics. The benefit of having disintegration time become independent of compression force in the excipient system allows for a greater robustness in the process for making a tablet.

In one embodiment, it was surprisingly found that the co-processed solid dispersions, excipient systems and formulations of the present invention are highly compactable and when compressed into solid dosage forms demonstrate uniform densification, low friability at low pressures, and/or relatively constant low disintegration times at various hardnesses. In one embodiment, the solid dosage forms of the present invention demonstrate superior organoleptics, fast disintegration, and/or good tablet robustness in chewable and oral dispersible tablet applications.

In one embodiment, the present invention relates to highly compactable and durable direct compression solid dispersions and excipient systems comprising co-processed carbohydrates, some of which have different solubilities, and form a microcrystalline plate structure, and formulations produced therefrom, which formulations are directly compressible into solid dosage forms, some of which demonstrate superior organoleptics, fast disintegration, and/or good robustness. In one embodiment, the present invention relates to highly compactable and durable direct compression solid dispersions and excipient systems comprising co-processed carbohydrates, some of which have different carbohydrate concentrations, and form a microcrystalline plate structure. In one embodiment, the present invention also includes, but is not limited to, the solid dosage forms produced by directly compressing the co-processed solid dispersion and/or excipient system.

In one embodiment, the present invention also relates to solid dispersions of co-processed carbohydrates that form particles having a microcrystalline plate structure, and that produce formulations that are directly compressible into solid dosage forms.

In one embodiment, the microcrystalline plate structure of the co-processed carbohydrates of the solid dispersions of the present invention allow for the production of solid dosage forms having uniform densification, low friability at low pressures, and/or relatively constant low disintegration times at various hardnesses.

In some embodiments, solid dosage forms of the present invention exhibit one or more of superior functionality such as tabletability, organoleptic characteristics, disintegration time, and a decreased sensitivity to compaction pressures; an increase in compaction pressure may result in a favorable decrease in friability and a surprisingly low increase in disintegration time. In some embodiments, an excipient system of the present invention is pH-independent. In some embodiments, an excipient system of the present invention is water dispersible.

Disintegration times related to excipient systems, pharmaceutical formulations and solid dosage forms of the present invention may be measured according to USP 32, Chapter 701. Friability related to excipient systems, pharmaceutical formulations and solid dosage forms of the present invention may be measured according to USP 32, Chapter 1216. Tablet breaking force related to excipient systems, pharmaceutical formulations and solid dosage forms of the present invention may be measured according to USP 32, Chapter 1217. Oral disintegration time may be measured as is considered the time taken for 1 orally-disintegrating tablet to disintegrate in the oral cavity of a panelist, as measured from the time of placement of the tablet until the time of perception of complete disintegration has occurred, as determined by the panelist. A set of 10 panelist's (n=10) observations will be used to calculate a mean and standard deviation of the oral disintegration time.

The present invention is described herein using several definitions, as set forth below and throughout the application.

DEFINITIONS

The term "about" will be understood by persons of ordinary skill in the art and will vary to some extent on the context in which it is used. If there are uses of the term which are not clear to persons of ordinary skill in the art given the context in which it is used, "about" shall mean up to plus or minus 10% of the particular value.

The phrase "completely dissolve or disintegrate" used in the context of the present invention, means that the solid dosage form dissolves or disintegrates to an extent that the patient believes the solid dosage form to be completely dissolved or disintegrated. That is, the patient can no longer detect any significant lumps or large particles of the original solid dosage form. Instead, at the point in time when the solid dosage from has completely dissolved or disintegrated in the oral cavity of the patient, the solid dosage form preferably has a creamy and pleasant mouthfeel that is conducive to swallowing.

The terms "solid dosage form," "tablet," and "solid preparation" are used synonymously within the context of the present invention. These terms should be construed to include a compacted or compressed powder composition obtained by compressing or otherwise forming the composition to form a solid having a defined shape.

The term "directly compressible" means that the composition can be compressed into tablet form on standard tabletting machines (including, but non limited to high speed tabletting machines) using standard (i.e., without any specially machined, shaped or coated surfaces) punches and dies, without any significant amount of the composition adhering to the punches and dies.

The term "oral cavity" should be construed to include, but should not be limited to the buccal cavity.

The term "co-processed carbohydrate" means the processing of at least two carbohydrates together to make a single product. For example, mannitol and sorbitol may be co-spray dried by first preparing a single solution of mannitol and sorbitol. Another example includes the co-granulation of mannitol and sorbitol.

The term "microcrystalline plate structure" means layers of crystalline and/or eutectic amorphous deposits, preferably planar plates and most preferably laminar planar plates. Microplate layers have a thickness of less than 5 microns, preferably less than 3 microns and most preferably less than 1 micron. Microcrystalline plates are mainly made up of 0% of a crystalline core, preferably 10% of a crystalline core, and most preferably 99.5% of a crystalline core and 100% of a eutectic mixture preferably greater than 90% of a eutectic mixture and most preferably greater than 0.5% of a eutectic mixture.

The term "solid dispersion" means a solid product consisting of a continuous phase (the dispersant), and a dispersed phase, in which the solid dispersion includes miscible components of different solubilities and/or concentrations. The dispersed phase can be also a continuous phase if the dispersant is a fully molecularly miscible eutectic with the dispersant, a discontinuous partially miscible eutectic, or a mixture of structured crystalline, or amorphous components incorporated into a fused structure in which the melting point of the solid dispersion is not lowered more than 5° C. from the melting point of the dispersant and the solid dispersion's heat of fusion is not reduced by more than 40 J/gm from the heat of fusion of the dispersant.

The term "solid layered dispersion" means a solid dispersion structured in layers. The primary and most significant layer is a crystalline or firm first layer or core. This layer develops first based on saturation conditions or is added as a suspended particle, followed by a crystallization or co-crystallization of the dispersant with the next most insoluble dispersed phase. This can be followed by a third or fourth layer or more dispersed components co-crystallizing, thus containing the core material and previous dispersed component(s).

The term "formulation" shall be construed to include a solid dispersion and/or excipient system plus an active ingredient, lubricant, optionally a disintegrant, optionally a glidant, optionally a sweetener, optionally a flavor, optionally a color, and optionally other excipients.

It has been discovered that the existing processes, products, or systems directed towards rapid disintegration or dissolution in the mouth have limitations in certain aspects. Specifically, until now it has been difficult to produce a tablet at low compression forces that is robust (e.g., low friability, low ejection forces, sufficient hardness) enough to be processed in high speed tabletting machines, especially at low compression pressures, and shipped in low cost packages, and at the same time retain rapid disintegration or dissolution properties. This is especially obvious when producing a tablet having high doses of active pharmaceutical ingredients (APIs) or when producing a tablet having APIs coated with different polymers, waxes, and the like for taste-masking, API protection, sustained release, and/or controlled release purposes.

In one embodiment, an advantage of the solid dispersions, excipient systems and formulations of the present invention is that they can be formed into high quality tablets on standard tabletting machines (including high speed tabletting machines such as those made by Killian or Korsh, capable of producing at least 75,000 tablets per hour) using standard punches and dies. The "standard" punches and dies referred to above are far less expensive to produce and maintain than the coated (e.g., teflon-coated) punches and dies used to produce tablets from formulations that are sticky or difficult to compress.

In one embodiment, the present invention overcomes these limitations by producing solid dispersions of co-processed carbohydrates with different solubilities. In one embodiment, the present invention overcomes these limitations by producing solid dispersions of co-processed carbohydrates with different concentrations. In one embodiment, the present invention overcomes these limitations by producing solid dispersions of co-processed carbohydrates with a microcrystalline plate structure. In one embodiment, the present invention overcomes these limitations by producing solid dispersions of co-processed carbohydrates with different solubilities, and with a microcrystalline plate structure. In one embodiment, the present invention overcomes these limitations by producing solid dispersions of co-processed carbohydrates with different concentrations, and with a microcrystalline plate structure. In one embodiment, the solid dispersion of the present invention formed from the co-processing of two or more carbohydrates is characterized by a single peak of a DSC (Differential Scanning Calorimeter) measurement.

In one embodiment, the microcrystalline plate structure of the solid dispersion allows for the production of solid dosage forms having uniform densification, low friability at low compression pressures, and/or relatively constant low disintegration times at various hardnesses. In one embodiment, the solid dispersion of the present invention ultimately produces a formulation that is compressible into a tablet. This tablet is robust enough to withstand stress of handling during production, packaging and transportation, without special processing or handling, while retaining rapid disintegration or dissolution properties and/or superior organoleptic properties like creamy smooth mouthfeel without any grittiness in the oral cavity. Further, in one embodiment, the present invention allows robust tablets to be made without cracking the coating of API's, where the integrity of the coating is critical for taste and/or controlled release or enteric functionality.

Carbohydrate Mixture

Carbohydrates useful in the present invention include, but are not limited to polyols and sugars. Suitable polyols may include but are not limited to sugar alcohols of the general formula $CH_2OH-(CHOH)_n-CH_2OH$, where n is 2 to 6, and preferably 3 to 6, and their dimeric anhydrides. In some embodiments, the polyols include, but are not limited to sorbitol, mannitol, xylitol, erythritol, maltitol, lactitol, isomalt, and mixtures thereof. In some embodiments, sugars include but are not limited to lactose, fructose, dextrose, sucrose, maltose, and mixtures thereof. In some embodiments, suitable sugars include but are not limited to xylose, melted over maltose and xylose melted over sucrose. In some embodiments, the solid dispersion does not include xylitol.

Components

The mannitol portion of the solid dispersion or excipient system can be from any source, such as MANNOGEM™ powder (SPI Pharma, Inc., Wilmington, Del.). Other sources of mannitol powder include GETEC Mannitol powder (BRAZIL), and PEARLITOL™ (Roquette, FRANCE).

The maltitol portion of an excipient system can be from any source, such as MR20 Amalty (Towa Chemical Industry Co., Ltd., Tokyo, JAPAN), Matlisorb® (Roquette, France) or Maltidex™ (Cargill, Inc.)

The sorbitol portion of the solid dispersion or excipient system can be from any source, such as Neosorb® (Roquette, FRANCE) or Sorbidex™ (Cargill, Inc.).

In some embodiments, a solid dispersion includes a first carbohydrate and a second carbohydrate. In some embodiments, the first carbohydrate includes a polyol. In some embodiments, the second carbohydrate includes a polyol. In some embodiments, the first carbohydrate includes a sugar. In some embodiments, the second carbohydrate includes a sugar. In some embodiments, a solid dispersion of the present invention includes about 80 wt % to about 99.5 wt % first carbohydrate and about 0.5 wt % to about 20 wt % second carbohydrate. In some embodiments, a solid dispersion includes about 80 wt % first carbohydrate; about 80.5 wt % first carbohydrate; about 81 wt % first carbohydrate; about 81.5 wt % first carbohydrate; about 82 wt % first carbohydrate; about 82.5 wt % first carbohydrate; about 83 wt % first carbohydrate; about 83.5 wt % first carbohydrate; about 84 wt % first carbohydrate; about 84.5 wt % first carbohydrate; about 85 wt % first carbohydrate; about 85.5 wt % first carbohydrate; about 86 wt % first carbohydrate; about 86.5 wt % first carbohydrate; about 87 wt % first carbohydrate; about 87.5 wt % first carbohydrate; about 88 wt % first carbohydrate; about 88.5 wt % first carbohydrate; about 89 wt % first carbohydrate; about 89.5 wt % first carbohydrate; about 90 wt % first carbohydrate; about 90.5 wt % first carbohydrate; about 91 wt % first carbohydrate; about 91.5 wt % first carbohydrate; about 92 wt % first carbohydrate; about 92.5 wt % first carbohydrate; about 93 wt % first carbohydrate; about 93.5 wt % first carbohydrate; about 94 wt % first carbohydrate; about 94.5 wt % first carbohydrate; about 95 wt % first carbohydrate; about 95.5 wt % first carbohydrate; about 96 wt % first carbohydrate; about 96.5 wt % first carbohydrate; about 97 wt % first carbohydrate; about 97.5 wt % first carbohydrate; about 98.5 wt % first carbohydrate; about 99 wt % first carbohydrate; or about 99.5 wt % first carbohydrate. In some embodiments, a solid dispersion includes about 0.5 wt % second carbohydrate; about 1 wt % second carbohydrate; about 1.5 wt % second carbohydrate; about 2 wt % second carbohydrate; about 2.5 wt % second carbohydrate; about 3 wt % second carbohydrate; about 3.5 wt % second carbohydrate; about 4 wt % second carbohydrate; about 4.5 wt % second carbohydrate; about 5 wt % second carbohydrate; about 5.5 wt % second carbohydrate; about 6 wt % second carbohydrate; about 6.5 wt % second carbohydrate; about 7 wt % second carbohydrate; about 7.5 wt % second carbohydrate; about 8 wt % second carbohydrate; about 8.5 wt % second carbohydrate; about 9 wt % second carbohydrate; about 9.5 wt % second carbohydrate; about 10 wt % second carbohydrate; about 10.5 wt % second carbohydrate; about 11 wt % second carbohydrate; about 11.5 wt % second carbohydrate; about 12 wt % second carbohydrate; about 12.5 wt % second carbohydrate; about 13 wt % second carbohydrate; about 13.5 wt % second carbohydrate; about 14 wt % second carbohydrate; about 14.5 wt % second carbohydrate; about 15 wt % second carbohydrate; about 15.5 wt % second carbohydrate; about 16 wt % second carbohydrate; about 16.5 wt % second carbohydrate; about 17 wt % second carbohydrate; about 17.5 wt % second carbohydrate; about 18.5 wt % second carbohydrate; about 19 wt % second carbohydrate; about 19.5 wt % second carbohydrate; or about 20 wt % second carbohydrate.

In some embodiments, the ratio of first carbohydrate:second carbohydrate can range from about 99:1 to about 70:30. In some embodiments, the ratio of first carbohydrate:second carbohydrate can range from about 99:1 to about 80:20; about 99:1 to about 85:15; about 99:1 to about 86:14; about 99:1 to about 87:13; about 99:1 to about 88:12; about 99:1 to about 89:11; about 99:1 to about 90:10; about 99:1 to about 91:9. In some embodiments, the first carbohydrate to second carbohydrate ratio is about 80:20; about 85:15; about 87:13; about 88:12; about 89:11; about 90:10, about 91:9; about 92:8; about 93:7; about 96:4; about 97:3; about 98:2; or about 99:1.

In some embodiments, a solid dispersion of the present invention includes about 70 wt % to about 99.5 wt % mannitol and about 0.5 wt % to about 30 wt % maltitol. In some embodiments, an excipient system includes about 70 wt % mannitol; about 70.5 wt %; about 71 wt %; about 71.5 wt %; about 72 wt %; about 72.5 wt %; about 73 wt %; about 73.5 wt %; about 74 wt %; about 74.5 wt %; about 75 wt %; about 75.5 wt %; about 76 wt %; about 76.5 wt %; about 77 wt %; about 77.5 wt %; about 78 wt %; about 78.5 wt %; about 79 wt %; about 79.5 wt %; about 80 wt % mannitol; about 80.5 wt % mannitol; about 81 wt % mannitol; about 81.5 wt % mannitol; about 82 wt % mannitol; about 82.5 wt % mannitol; about 83 wt % mannitol; about 83.5 wt % mannitol; about 84 wt % mannitol; about 84.5 wt % mannitol; about 85 wt % mannitol; about 85.5 wt % mannitol; about 86 wt % mannitol; about 86.5 wt % mannitol; about 87 wt % mannitol; about 87.5 wt % mannitol; about 88 wt % mannitol; about 88.5 wt % mannitol; about 89 wt % mannitol; about 89.5 wt % mannitol; about 90 wt % mannitol; about 90.5 wt % mannitol; about 91 wt % mannitol; about 91.5 wt % mannitol; about 92 wt % mannitol; about 92.5 wt % mannitol; about 93 wt % mannitol; about 93.5 wt % mannitol; about 94 wt % mannitol; about 94.5 wt % mannitol; about 95 wt % mannitol; about 95.5 wt % mannitol; about 96 wt % mannitol; about 96.5 wt % mannitol; about 97 wt % mannitol; about 97.5 wt % mannitol; about 98.5 wt % mannitol; about 99 wt % mannitol; or about 99.5 wt % mannitol. In some embodiments, a solid dispersion includes about 0.5 wt % maltitol; about 1 wt % maltitol; about 1.5 wt % maltitol; about 2 wt % maltitol; about 2.5 wt % maltitol; about 3 wt % maltitol; about 3.5 wt % maltitol; about 4 wt % maltitol; about 4.5 wt % maltitol; about 5 wt % maltitol; about 5.5 wt % maltitol; about 6 wt % maltitol; about 6.5 wt % maltitol; about 7 wt % maltitol; about 7.5 wt % maltitol; about 8 wt % maltitol; about 8.5 wt % maltitol; about 9 wt % maltitol; about 9.5 wt % maltitol; about 10 wt % maltitol; about 10.5 wt % maltitol; about 11 wt % maltitol; about 11.5 wt % maltitol; about 12 wt % maltitol; about 12.5 wt % maltitol; about 13 wt % maltitol; about 13.5 wt % maltitol; about 14 wt % maltitol; about 14.5 wt % maltitol; about 15 wt % maltitol; about 15.5 wt % maltitol; about 16 wt % maltitol; about 16.5 wt % maltitol; about 17 wt % maltitol; about 17.5 wt % maltitol; about 18.5 wt % maltitol; about 19 wt % maltitol; about 19.5 wt % maltitol; about 20 wt % maltitol; about 20.5 wt %; about 21 wt %; about 21.5 wt %; about 22 wt %; about 22.5 wt %; about 23 wt %; about 23.5 wt %; about 24 wt %; about 24.5 wt %; about 25 wt %; about 25.5 wt %, about 26 wt %; about 26 wt %; about 26.5 wt %; about 27 wt %; about 27.5 wt %; about 28 wt %; about 28.5 wt %; about 29 wt %; about 29.5 wt %; or about 30 wt %.

In some embodiments, the ratio of mannitol:maltitol can range from about 99:1 to about 70:30. In some embodiments, the ratio of mannitol:maltitol can range from about 99:1 to about 80:20; about 99:1 to about 85:15; about 99:1 to about 86:14; about 99:1 to about 87:13; about 99:1 to about 88:12; about 99:1 to about 89:11; about 99:1 to about 90:10; about 99:1 to about 91:9. In some embodiments, the mannitol to maltitol ratio is about 80:20; about 85:15; about 87:13; about 88:12; about 89:11; about 90:10, about 91:9; about 92:8; about 93:7; about 96:4; about 97:3; about 98:2; or about 99:1.

In some embodiments, a solid dispersion of the present invention includes about 80 wt % to about 99.5 wt % mannitol and about 0.5 wt % to about 20 wt % isomalt. In some embodiments, an excipient system includes about 80 wt % mannitol; about 80.5 wt % mannitol; about 81 wt % mannitol; about 81.5 wt % mannitol; about 82 wt % mannitol; about 82.5 wt % mannitol; about 83 wt % mannitol; about 83.5 wt % mannitol; about 84 wt % mannitol; about 84.5 wt % mannitol; about 85 wt % mannitol; about 85.5 wt % mannitol; about 86 wt % mannitol; about 86.5 wt % mannitol; about 87 wt % mannitol; about 87.5 wt % mannitol; about 88 wt % mannitol; about 88.5 wt % mannitol; about 89 wt % mannitol; about 89.5 wt % mannitol; about 90 wt % mannitol; about 90.5 wt % mannitol; about 91 wt % mannitol; about 91.5 wt % mannitol; about 92 wt % mannitol; about 92.5 wt % mannitol; about 93 wt % mannitol; about 93.5 wt % mannitol; about 94 wt % mannitol; about 94.5 wt % mannitol; about 95 wt % mannitol; about 95.5 wt % mannitol; about 96 wt % mannitol; about 96.5 wt % mannitol; about 97 wt % mannitol; about 97.5 wt % mannitol; about 98.5 wt % mannitol; about 99 wt % mannitol; or about 99.5 wt % mannitol. In some embodiments, an excipient system includes about 0.5 wt % isomalt; about 1 wt % isomalt; about 1.5 wt % isomalt; about 2 wt % isomalt; about 2.5 wt % isomalt; about 3 wt % isomalt; about 3.5 wt % isomalt; about 4 wt % isomalt; about 4.5 wt % isomalt; about 5 wt % isomalt; about 5.5 wt % isomalt; about 6 wt % isomalt; about 6.5 wt % isomalt; about 7 wt % isomalt; about 7.5 wt % isomalt; about 8 wt % isomalt; about 8.5 wt % isomalt; about 9 wt % isomalt; about 9.5 wt % isomalt; about 10 wt % isomalt; about 10.5 wt % isomalt; about 11 wt % isomalt; about 11.5 wt % isomalt; about 12 wt % isomalt; about 12.5 wt % isomalt; about 13 wt % isomalt; about 13.5 wt % isomalt; about 14 wt % isomalt; about 14.5 wt % isomalt; about 15 wt % isomalt; about 15.5 wt % isomalt; about 16 wt % isomalt; about 16.5 wt % isomalt; about 17 wt % isomalt; about 17.5 wt % isomalt; about 18.5 wt % isomalt; about 19 wt % isomalt; about 19.5 wt % isomalt; or about 20 wt % isomalt.

In some embodiments, the ratio of mannitol:isomalt can range from about 99:1 to about 70:30. In some embodiments, the ratio of mannitol:isomalt can range from about 99:1 to about 80:20; about 99:1 to about 85:15; about 99:1 to about 86:14; about 99:1 to about 87:13; about 99:1 to about 88:12; about 99:1 to about 89:11; about 99:1 to about 90:10; about 99:1 to about 91:9. In some embodiments, the mannitol to isomalt ratio is about 80:20; about 85:15; about 87:13; about 88:12; about 89:11; about 90:10, about 91:9; about 92:8; about 93:7; about 96:4; about 97:3; about 98:2; or about 99:1.

In some embodiments, a solid dispersion includes a first carbohydrate, a second carbohydrate, and a third carbohydrate. In some embodiments, the first carbohydrate includes a polyol. In some embodiments, the second carbohydrate includes a polyol. In some embodiments, the third carbohydrate includes a polyol. In some embodiments, the first carbohydrate includes a sugar. In some embodiments, the second carbohydrate includes a sugar. In some embodiments, the third carbohydrate includes a sugar. In some embodiments, a solid dispersion includes about 80 wt % to about 99.5 wt % first carbohydrate, about 0.5 wt % to about 20 wt % second carbohydrate, and about 0.5 wt % to about 20 wt % third carbohydrate. In some embodiments, a solid dispersion includes about 80 wt % first carbohydrate; about 80.5 wt % first carbohydrate; about 81 wt % first carbohydrate; about 81.5 wt % first carbohydrate; about 82 wt % first carbohydrate; about 82.5 wt % first carbohydrate; about 83 wt % first carbohydrate; about 83.5 wt % first carbohydrate; about 84 wt % first carbohydrate; about 84.5 wt % first carbohydrate; about 85 wt % first carbohydrate; about 85.5 wt % first carbohydrate; about 86 wt % first carbohydrate; about 86.5 wt % first carbohydrate; about 87 wt % first carbohydrate; about 87.5 wt % first carbohydrate; about 88 wt % first carbohydrate; about 88.5 wt % first carbohydrate; about 89 wt % first carbohydrate; about 89.5 wt % first carbohydrate; about 90 wt % first carbohydrate; about 90.5 wt % first carbohydrate; about 91 wt % first carbohydrate; about 91.5 wt % first carbohydrate; about 92 wt % first carbohydrate; about 92.5 wt % first carbohydrate; about 93 wt % first carbohydrate; about 93.5 wt % first carbohydrate; about 94 wt % first carbohydrate; about 94.5 wt % first carbohydrate; about 95 wt % first carbohydrate; about 95.5 wt % first carbohydrate; about 96 wt % first carbohydrate; about 96.5 wt % first carbohydrate; about 97 wt % first carbohydrate; about 97.5 wt % first carbohydrate; about 98.5 wt % first carbohydrate; about 99 wt % first carbohydrate; or about 99.5 wt % first carbohydrate.

In some embodiments, a solid dispersion includes greater than 94 wt % first carbohydrate. In some embodiments, a solid dispersion includes greater than 94.5 wt % first carbohydrate. In some embodiments, a solid dispersion includes greater than 95 wt % first carbohydrate. In some embodiments, a solid dispersion includes greater than 95.5 wt % first carbohydrate. In some embodiments, a solid dispersion includes greater than 96 wt % first carbohydrate. In some embodiments, a solid dispersion includes greater than 96.5 wt % first carbohydrate. In some embodiments, a solid dispersion includes greater than 97 wt % first carbohydrate. In some embodiments, a solid dispersion includes greater than 97.5 wt % first carbohydrate. In some embodiments, a solid dispersion includes greater than 98 wt % first carbohydrate. In some embodiments, a solid dispersion includes greater than 98.5 wt % first carbohydrate. In some embodiments, a solid dispersion includes greater than 99 wt % first carbohydrate. In some embodiments, a solid dispersion includes greater than 99.5 wt % first carbohydrate.

In some embodiments, a solid dispersion includes about 0.5 wt % second carbohydrate; about 1 wt % second carbohydrate; about 1.5 wt % second carbohydrate; about 1.7 wt % second carbohydrate; about 2 wt % second carbohydrate; about 2.3 wt % second carbohydrate; about 2.5 wt % second carbohydrate; about 3 wt % second carbohydrate; about 3.5 wt % second carbohydrate; about 4 wt % second carbohydrate; about 4.5 wt % second carbohydrate; about 5 wt % second carbohydrate; about 5.5 wt % second carbohydrate; about 6 wt % second carbohydrate; about 6.5 wt % second carbohydrate; about 7 wt % second carbohydrate; about 7.5 wt % second carbohydrate; about 8 wt % second carbohydrate; about 8.5 wt % second carbohydrate; about 9 wt % second carbohydrate; about 9.5 wt % second carbohydrate; about 10 wt % second carbohydrate; about 10.5 wt % second carbohydrate; about 11 wt % second carbohydrate; about 11.5 wt % second carbohydrate; about 12 wt % second carbohydrate; about 12.5 wt % second carbohydrate; about 13 wt % second carbohydrate; about 13.5 wt % second carbohydrate; about 14 wt % second carbohydrate; about 14.5 wt % second carbohydrate; about 15 wt % second carbohydrate; about 15.5 wt % second carbohydrate; about 16 wt % second carbohydrate; about 16.5 wt % second carbohydrate; about 17 wt % second carbohydrate; about 17.5 wt % second carbohydrate; about 18.5 wt % second carbohydrate; about 19 wt % second carbohydrate; about 19.5 wt % second carbohydrate; or about 20 wt % second carbohydrate. In some embodiments, an excipient system includes about 0.5 wt % third carbohydrate; about 1 wt % third carbohydrate; about 1.5 wt % third carbohydrate; about 1.7 wt % third carbohydrate; about 2 wt % third carbohydrate; about 2.3 wt % third carbohydrate; about 2.5 wt % third carbohydrate; about 3 wt % third carbohydrate; about 3.5 wt % third carbohydrate; about 4 wt % third carbohydrate; about 4.5 wt % third carbohydrate; about 5 wt % third carbohydrate; about 5.5 wt % third carbohydrate; about 6 wt % third carbohydrate; about 6.5 wt % third carbohydrate; about 7 wt % third carbohydrate; about 7.5 wt % third carbohydrate; about 8 wt % third carbohydrate; about 8.5 wt % third carbohydrate; about 9 wt % third carbohydrate; about 9.5 wt % third carbohydrate; about 10 wt % third carbohydrate; about 10.5 wt % third carbohydrate; about 11 wt % third carbohydrate; about 11.5 wt % third carbohydrate; about 12 wt % third carbohydrate; about 12.5 wt % third carbohydrate; about 13 wt % third carbohydrate; about 13.5 wt % third carbohydrate; about 14 wt % third carbohydrate; about 14.5 wt % third carbohydrate; about 15 wt % third carbohydrate; about 15.5 wt % third carbohydrate; about 16 wt % third carbohydrate; about 16.5 wt % third carbohydrate; about 17 wt % third carbohydrate; about 17.5 wt % third carbohydrate; about 18.5 wt % third carbohydrate; about 19 wt % third carbohydrate; about 19.5 wt % third carbohydrate; or about 20 wt % third carbohydrate.

In some embodiments, a solid dispersion includes about 80 wt % to about 99.5 wt % mannitol, about 0.5 wt % to about 20 wt % maltitol, and about 0.5 wt % to about 20 wt % sorbitol. In some embodiments, a solid dispersion includes about 80 wt % mannitol; about 80.5 wt % mannitol; about 81 wt % mannitol; about 81.5 wt % mannitol; about 82 wt % mannitol; about 82.5 wt % mannitol; about 83 wt % mannitol; about 83.5 wt % mannitol; about 84 wt % mannitol; about 84.5 wt % mannitol; about 85 wt % mannitol; about 85.5 wt % mannitol; about 86 wt % mannitol; about 86.5 wt % mannitol; about 87 wt % mannitol; about 87.5 wt % mannitol; about 88 wt % mannitol; about 88.5 wt % mannitol; about 89 wt % mannitol; about 89.5 wt % mannitol; about 90 wt % mannitol; about 90.5 wt % mannitol; about 91 wt % mannitol; about 91.5 wt % mannitol; about 92 wt % mannitol; about 92.5 wt % mannitol; about 93 wt % mannitol; about 93.5 wt % mannitol; about 94 wt % mannitol; about 94.5 wt % mannitol; about 95 wt % mannitol; about 95.5 wt % mannitol; about 96 wt % mannitol; about 96.5 wt % mannitol; about 97 wt % mannitol; about 97.5 wt % mannitol; about 98.5 wt % mannitol; about 99 wt % mannitol; or about 99.5 wt % mannitol. In some embodiments, a solid dispersion includes about 0.5 wt % maltitol; about 1 wt % maltitol; about 1.5 wt % maltitol; about 1.7 wt % maltitol; about 2 wt % maltitol; about 2.5 wt % maltitol; about 3 wt % maltitol; about 3.5 wt % maltitol; about 4 wt % maltitol; about 4.5 wt % maltitol; about 5 wt % maltitol; about 5.5 wt % maltitol; about 6 wt % maltitol; about 6.5 wt % maltitol; about 7 wt % maltitol; about 7.5 wt % maltitol; about 8 wt % maltitol; about 8.5 wt % maltitol; about 9 wt % maltitol; about 9.5 wt % maltitol; about 10 wt % maltitol; about 10.5 wt % maltitol; about 11 wt % maltitol; about 11.5 wt % maltitol; about 12 wt % maltitol; about 12.5 wt % maltitol; about 13 wt % maltitol; about 13.5 wt % maltitol; about 14 wt % maltitol; about 14.5 wt % maltitol; about 15 wt % maltitol; about 15.5 wt % maltitol; about 16 wt % maltitol; about 16.5 wt % maltitol; about 17 wt % maltitol; about 17.5 wt % maltitol; about 18.5 wt % maltitol; about 19 wt % maltitol; about 19.5 wt % maltitol; or about 20 wt % maltitol. In some embodiments, an excipient system includes about 0.5 wt % sorbitol; about 1 wt % sorbitol; about 1.5 wt % sorbitol; about 2 wt % sorbitol; about 2.3 wt % sorbitol; about 2.5 wt % sorbitol; about 3 wt % sorbitol; about 3.5 wt % sorbitol; about 4 wt % sorbitol; about 4.5 wt % sorbitol; about 5 wt % sorbitol; about 5.5 wt % sorbitol; about 6 wt % sorbitol; about 6.5 wt % sorbitol; about 7 wt % sorbitol; about 7.5 wt % sorbitol; about 8 wt % sorbitol; about 8.5 wt % sorbitol; about 9 wt % sorbitol; about 9.5 wt % sorbitol; about 10 wt % sorbitol; about 10.5 wt % sorbitol; about 11 wt % sorbitol; about 11.5 wt % sorbitol; about 12 wt % sorbitol; about 12.5 wt % sorbitol; about 13 wt % sorbitol; about 13.5 wt % sorbitol; about 14 wt % sorbitol; about 14.5 wt % sorbitol; about 15 wt % sorbitol; about 15.5 wt % sorbitol; about 16 wt % sorbitol; about 16.5 wt % sorbitol; about 17 wt % sorbitol; about 17.5 wt % sorbitol; about 18.5 wt % sorbitol; about 19 wt % sorbitol; about 19.5 wt % sorbitol; or about 20 wt % sorbitol.

In some embodiments, a solid dispersion includes about 80 wt % to about 99.5 wt % mannitol, about 0.5 wt % to about 20 wt % isomalt, and about 0.5 wt % to about 20 wt % sorbitol. In some embodiments, a solid dispersion includes about 80 wt % mannitol; about 80.5 wt % mannitol; about 81 wt % mannitol; about 81.5 wt % mannitol; about 82 wt % mannitol; about 82.5 wt % mannitol; about 83 wt % mannitol; about 83.5 wt % mannitol; about 84 wt % mannitol; about 84.5 wt % mannitol; about 85 wt % mannitol; about 85.5 wt % mannitol; about 86 wt % mannitol; about 86.5 wt % mannitol; about 87 wt % mannitol; about 87.5 wt % mannitol; about 88 wt % mannitol; about 88.5 wt % mannitol; about 89 wt % mannitol; about 89.5 wt % mannitol; about 90 wt % mannitol; about 90.5 wt % mannitol; about 91 wt % mannitol; about 91.5 wt % mannitol; about 92 wt % mannitol; about 92.5 wt % mannitol; about 93 wt % mannitol; about 93.5 wt % mannitol; about 94 wt % mannitol; about 94.5 wt % mannitol; about 95 wt % mannitol; about 95.5 wt % mannitol; about 96 wt % mannitol; about 96.5 wt % mannitol; about 97 wt % mannitol; about 97.5 wt % mannitol; about 98.5 wt % mannitol; about 99 wt % mannitol; or about 99.5 wt % mannitol. In some embodiments, a solid dispersion includes about 0.5 wt % isomalt; about 1 wt % isomalt; about 1.5 wt % isomalt; about 1.7 wt % isomalt; about 2 wt % isomalt; about 2.5 wt % isomalt; about 3 wt % isomalt; about 3.5 wt % isomalt; about 4 wt % isomalt; about 4.5 wt % isomalt; about 5 wt % isomalt; about 5.5 wt % isomalt; about 6 wt % isomalt; about 6.5 wt % isomalt; about 7 wt % isomalt; about 7.5 wt % isomalt; about 8 wt % isomalt; about 8.5 wt % isomalt; about 9 wt % isomalt; about 9.5 wt % isomalt; about 10 wt % isomalt; about 10.5 wt % isomalt; about 11 wt % isomalt; about 11.5 wt % isomalt; about 12 wt % isomalt; about 12.5 wt % isomalt; about 13 wt % isomalt; about 13.5 wt % isomalt; about 14 wt % isomalt; about 14.5 wt % isomalt; about 15 wt % isomalt; about 15.5 wt % isomalt; about 16 wt % isomalt; about 16.5 wt % isomalt; about 17 wt % isomalt; about 17.5 wt % isomalt; about 18.5 wt % isomalt; about 19 wt % isomalt; about 19.5 wt % isomalt; or about 20 wt % isomalt. In some embodiments, an excipient system includes about 0.5 wt % sorbitol; about 1 wt % sorbitol; about 1.5 wt % sorbitol; about 2 wt % sorbitol; about 2.3 wt % sorbitol; about 2.5 wt % sorbitol; about 3 wt % sorbitol; about 3.5 wt % sorbitol; about 4 wt % sorbitol; about 4.5 wt % sorbitol; about 5 wt % sorbitol; about 5.5 wt % sorbitol; about 6 wt % sorbitol; about 6.5 wt % sorbitol; about 7 wt % sorbitol; about 7.5 wt % sorbitol; about 8 wt % sorbitol; about 8.5 wt % sorbitol; about 9 wt % sorbitol; about 9.5 wt % sorbitol; about 10 wt % sorbitol; about 10.5 wt % sorbitol; about 11 wt % sorbitol; about 11.5 wt % sorbitol; about 12 wt % sorbitol; about 12.5 wt % sorbitol; about 13 wt % sorbitol; about 13.5 wt % sorbitol; about 14 wt % sorbitol; about 14.5 wt % sorbitol; about 15 wt % sorbitol; about 15.5 wt % sorbitol; about 16 wt % sorbitol; about 16.5 wt % sorbitol; about 17 wt % sorbitol; about 17.5 wt % sorbitol; about 18.5 wt % sorbitol; about 19 wt % sorbitol; about 19.5 wt % sorbitol; or about 20 wt % sorbitol.

In some embodiments, a solid dispersion includes greater than 94 wt % mannitol. In some embodiments, a solid dispersion includes greater than 95 wt % mannitol. In some embodiments, a solid dispersion includes greater than 96 wt % mannitol. In some embodiments, a solid dispersion includes greater than 97 wt % mannitol. In some embodiments, a solid dispersion includes greater than 98 wt % mannitol. In some embodiments, a solid dispersion includes greater than 99 wt % mannitol.

In some embodiments, a solid dispersion includes less than 5 wt % maltitol. In some embodiments, a solid dispersion includes less than 4 wt % maltitol. In some embodiments, a solid dispersion includes less than 3 wt % maltitol. In some embodiments, a solid dispersion includes less than 2 wt % maltitol. In some embodiments, a solid dispersion includes less than 1 wt % maltitol. In some embodiments, a solid dispersion includes less than 0.75 wt % maltitol. In some embodiments, a solid dispersion includes less than 0.50 wt % maltitol. In some embodiments, a solid dispersion includes less than 0.25 wt % of maltitol.

In some embodiments, a solid dispersion includes less than 5 wt % isomalt. In some embodiments, a solid dispersion includes less than 4 wt % isomalt. In some embodiments, a solid dispersion includes less than 3 wt % isomalt. In some embodiments, a solid dispersion includes less than 2 wt % isomalt. In some embodiments, a solid dispersion includes less than 1 wt % isomalt.

In some embodiments, a solid dispersion includes less than 5 wt % lactitol. In some embodiments, a solid dispersion includes less than 4 wt % lactitol. In some embodiments, a solid dispersion includes less than 3 wt % lactitol. In some embodiments, a solid dispersion includes less than 2 wt % lactitol. In some embodiments, a solid dispersion includes less than 1 wt % lactitol. In some embodiments, a solid dispersion includes less than 0.75 wt % lactitol. In some embodiments, a solid dispersion includes less than 0.50 wt % lactitol. In some embodiments, a solid dispersion includes less than 0.25 wt % of lactitol.

In some embodiments, a solid dispersion includes less than 5 wt % sorbitol. In some embodiments, a solid dispersion includes less than 4 wt % sorbitol. In some embodiments, a solid dispersion includes less than 3 wt % sorbitol. In some embodiments, a solid dispersion includes less than 2 wt % sorbitol. In some embodiments, a solid dispersion includes less than 1 wt % sorbitol. In some embodiments, a solid dispersion includes less than 0.75 wt % sorbitol. In some embodiments, a solid dispersion includes less than 0.50 wt % sorbitol. In some embodiments, a solid dispersion includes less than 0.25 wt % of sorbitol.

In some embodiments, a solid dispersion includes greater than 90 wt % mannitol and two polyols. In some embodiments, a solid dispersion includes greater than 91 wt % mannitol and two polyols. In some embodiments, a solid dispersion includes greater than 92 wt % mannitol and two polyols. In some embodiments, a solid dispersion includes greater than 93 wt % mannitol and two polyols. In some embodiments, a solid dispersion includes greater than 94 wt % mannitol and two polyols. In some embodiments, a solid dispersion includes greater than 95 wt % mannitol and two polyols. In some embodiments, a solid dispersion includes greater than 96 wt % mannitol and two polyols. In some embodiments, a solid dispersion includes greater than 97 wt % mannitol and two polyols. In some embodiments, a solid dispersion includes greater than 98 wt % mannitol and two polyols. In some embodiments, a solid dispersion includes greater than 99 wt % mannitol and two polyols.

In some embodiments, a solid dispersion includes less than 5 wt % sorbitol and two polyols. In some embodiments, a solid dispersion includes less than 4 wt % sorbitol and two polyols. In some embodiments, a solid dispersion includes less than 3 wt % sorbitol and two polyols. In some embodiments, a solid dispersion includes less than 2 wt % sorbitol and two polyols. In some embodiments, a solid dispersion includes less than 1 wt % sorbitol and two polyols. In some embodiments, a solid dispersion includes less than 0.75 wt % sorbitol and two polyols. In some embodiments, a solid dispersion includes less than 0.50 wt % sorbitol and two polyols. In some embodiments, a solid dispersion includes less than 0.25 wt % sorbitol and two polyols.

In some embodiments, a solid dispersion includes less than 5 wt % maltitol and two polyols. In some embodiments, a solid dispersion includes less than 4 wt % maltitol and two polyols. In some embodiments, a solid dispersion includes less than 3 wt % maltitol and two polyols. In some embodiments, a solid dispersion includes less than 2 wt % maltitol and two polyols. In some embodiments, a solid dispersion includes less than 1 wt % maltitol and two polyols. In some embodiments, a solid dispersion includes less than 0.75 wt % maltitol and two polyols. In some embodiments, a solid dispersion includes less than 0.50 wt % maltitol and two polyols. In some embodiments, a solid dispersion includes less than 0.25 wt % maltitol and two polyols.

Methods of Making

Any suitable process may be used to manufacture a solid dispersion of at least two or at least three carbohydrates, including but not limited to spray drying, fluid bed, co-granulation or high shear mixing.

Co-Spray Dried

In some embodiments, the solid dispersion of at least two or at least three carbohydrates are co-spray dried. A suitable method of co-spray drying is described in U.S. Pat. No. 7,118,765, which is incorporated by reference herein in its entirety. Any spray dryer may be useful in the present invention. In some embodiments of the invention, an S1 Spray Fluid Bed Dryer with a 2.1 meter diameter is used (DRYTEC; Tonbridge, Kent, ENGLAND). The spray dryer operates by atomizing a liquid feed material in a stream of air or other gas. The main use of the spray drying equipment is drying but the equipment can also be used for agglomerating, congealing, encapsulation, cooling and/or conditioning the composition of the present invention. A flow diagram depicting the operation pattern of the fluid bed spray dryer is shown in FIG. 1.

Air for drying is heated by a heater 1 and enters the top of a drying chamber 4 through a hot air duct 8. A feed pump 2 delivers the liquid feed through feed line 3 to an atomizer which sprays the composition in fine droplets into a hot air stream entering the top of a drying chamber 4. This causes rapid drying due to the large liquid area exposed. In the present invention, one of several atomizers can be used. For example, a centrifugal driven atomizer, a two fluid nozzle using a jet of compressed air to atomize the feed, or a pressure nozzle atomizer can be used in the present invention.

An integrated fluid bed 10 is attached at the bottom of chamber 4. The fines and air leave from a side outlet 9 of the cone of drying chamber 4 to a cyclone 5. Cyclone 5 separates the fines from the air. The air is exhausted out through a bag filter 6. The fines are recycled to the top of drying chamber 4 into a wet zone 11 where agglomeration takes place, and drop into integrated fluid bed 10. The action of the fluidization by the hot air supplied to the fluid bed allows the coarser particles to dry further and the fines are taken away to cyclone 5.

The carbohydrate solution (for example, at least two polyols or at least three polyols) is then fed into the integrated spray fluid bed drying chamber unit under sealed conditions and a controlled stream of hot air at a temperature of about 200 degrees Celsius (° C.) dries the solution in the form of fine droplets. Once the desired particle size is achieved, the carbohydrate product is collected. Particle size can range from about 0.1 to 500 microns. In one embodiment of the present invention, at least 85% of the particles are about 100 microns or greater. In another embodiment of the present invention, at least 50% of the particles are about 100 microns or greater. The smaller particles ("fines") generated during this process are recycled back to the top of drying chamber 4 for further agglomeration.

In one embodiment, a spray dried mixture of 92% mannitol/8% maltitol was prepare on an Anhydro Micra-35 using an inlet temperature of 195° C., an outlet temp of 90 to 95° C., air flow of 32 kg/hr, a gas pressure drop of 2.6 psig, an atomization air flow at 4.1 kg/hr, an atomization air temperature of 60° C., an atomization air pressure of 39 psig, a chamber jacket temperature at 90° C., and a cyclone jacket surface temperature of 90° C. The spray rate of liquid was adjusted to maintain a 90° C. outlet temperature.

Co-Granulation

In some embodiments of the invention, a carbohydrate mixture of at least two or at least three carbohydrates is prepared by co-granulation.

Fluid Bed

In some embodiments, a solid dispersion of at least two or at least three carbohydrates is prepared with a fluid bed. In one example, a mannitol, maltitol, and sorbitol mixture may be prepared by adding 20 kg of milled 30 μm or smaller mannitol Vwm diameter powder (such as Getec, Roquette, etc) to a fluid bed (such as Fluid Air Model 50 L). A solution is made from 170 g maltitol and 80 g mannitol in 500 mL of water (solution A). A solution is also made from 170 g maltitol, 320 g mannitol, and 460 g of sorbitol in 2000 mL of water. (Solution B). With an inlet temperature of 80° C., mannitol powder bed is heated to 30° C., with an air volume of 140 SCFM. Then, Solution A may be sprayed on at a rate of 70 g/min, followed by Solution B at 70 to 150 g/min to obtain agglomerates. The product may then be dried at 80° C. and 140 SCFM until the product is less than 0.5% moisture.

High Shear

In some embodiments, a solid dispersion of at least two or at least three carbohydrates is prepared using high shear. In one example, a mixture of mannitol, maltitol, and sorbitol can be prepared by adding 20 kg of milled 30 μM or smaller mannitol Vwm diameter powder (such as Getec, Roquette, etc) and 170 g maltitol to a horizontal high shear mixer (such as Littleford 5 cu ft mixer—JH Day Cincinati Ohio). In some embodiments, solution is made from 170 g maltitol, 160 g mannitol, and 460 g sorbitol in 1000 mL water. The solution can then be added to the high shear mixer to granulate particles. If necessary, additional liquid may be added to obtain the size particles desired. Next, the particles can be dried at 80° C. and 140 SCFM in a fluid bed (such as Fluid Air Model 50L) until product is less than 0.5% moisture. The product can then be milled and screened to the appropriate particle size if necessary using, for example, a FitzMill Model D6 (Fitzpatrick Company) at 2000 RPM, and a screen and a Sweco screener using, for example, a USS 20 mesh screen.

Characteristics

In some embodiments, solid dispersions and/or excipient systems including at least two carbohydrates, such as mannitol and maltitol or isomalt, or at least three carbohydrates, such as mannitol, maltitol or isomalt, and sorbitol, demonstrate superior functionality such as tabletability, durability, organoleptic characteristics, disintegration time, and/or an advantageous decrease in sensitivity to the amount of compaction. For example, in some embodiments, an increased compaction pressure applied to the solid dispersion or excipient system results in a tablet with a more favorable friability value, increased hardness values, and surprisingly, only a slight increase in disintegration time. Such characteristics may be displayed for solid dispersions or excipient systems including co-granulated and/or spray dried carbohydrates.

In some embodiments, an excipient system including 90 wt % mannitol and 10 wt % maltitol has a hardness value of about 14 kP upon application of a 15 kN compression force. Such excipient system may have a friability value of about 0.20%. Such excipient system may have a disintegration time of less than about 10 minutes In some embodiments, an excipient system including 90 wt % mannitol and 10 wt % maltitol has a hardness value of about 32 kP upon application of a 30 kN compression force. Such excipient system may have a friability value of about 0.08%. Such excipient system may have a disintegration time of less than about 10 minutes.

In some embodiments, an excipient system including 99 wt % mannitol and 1 wt % maltitol has a hardness value of about 16 kP upon application of a 15 kN compression force. Such excipient system may have a friability value of about 0.14%. Such excipient system may have a disintegration time of less than about 8 minutes.

In some embodiments, an excipient system including 99 wt % mannitol and 1 wt % maltitol has a hardness value of about 22 kP upon application of a 30 kN compression force. Such excipient system may have a friability value of about 0.18%. Such excipient system may have a disintegration time of less than about 8 minutes.

In some embodiments, an excipient system including 96.5 wt % mannitol and 3.5 wt % maltitol has a hardness value of about 14 kP upon application of a 15 kN compression force. Such an excipient system may have a friability value of about 0.22%. Such an excipient system may have a disintegration time of less than about 6 minutes.

In some embodiments, an excipient system including 96.5 wt % mannitol and 3.5 wt % maltitol has a hardness value of about 28 kP upon application of a 30 kN compression force. Such an excipient system may have a friability value of about 0.22%. Such an excipient system may have a disintegration time of less than about 8 minutes.

In some embodiments, an excipient system including 96 wt % mannitol, 1.7 wt % maltitol, and 2.3 wt % sorbitol has a hardness value of about 22 kP upon application of a 13 kN compression force. Such an excipient system may have a friability value of about 0.11%.

In some embodiments, an excipient system including 96 wt % mannitol, 1.7 wt % maltitol and 2.3 wt % sorbitol has a hardness value of about 50 kP upon application of a 33 kN compression force. Such an excipient system may have a friability value of about 0.13%.

In some embodiments, an excipient system including 91.2 wt % mannitol, 6.5 wt % maltitol and 2.3 wt % sorbitol has a hardness value of about 18 kP upon application of a 13 kN compression force. Such an excipient system may have a friability value of about 0.20%.

In some embodiments, an excipient system including 91.2 wt % mannitol, 6.5 wt % maltitol and 2.3 wt % sorbitol has a hardness value of about 35 kP upon application of a 33 kN compression force. Such an excipient system may have a friability value of about 0.24%.

In some embodiments, an excipient system including 91.2 wt % mannitol, 2.3% sorbitol and 6.5 wt % maltitol has a hardness value of about 14 kP upon application of a 13 kN compression force. Such an excipient system may have a friability value of about 0.17%.

In some embodiments, an excipient system including 91.2 wt % mannitol, 2.3% sorbitol and 6.5 wt % maltitol has a hardness value of about 45 kP upon application of a 34 kN compression force. Such an excipient system may have a friability value of about 0.13%.

In some embodiments, the moisture content of the solid dispersion may be less than about 8%, less than about 5%, less than about 3%, less than about 2%, less than about 1% or less than about 0.5%. In one embodiment of the present invention, the moisture content of the solid dispersion is about 0.3%.

In some embodiments, the friability of the solid dispersion in powder form is about 15% to about 35%. In some embodiments, the friability of the solid dispersion in powder form is less than 35%, less than 30%, less than 25%, or less than 20%.

In some embodiments, the friability of the resulting compressed solid dispersion may be less than about 5%, less than about 4%, less than about 3%, less than about 2%, less than about 1%, less than about 0.5%, less than about 0.4%, less than about 0.3%, less than about 0.2%, or less than about 0.1%.

In some embodiments, the compactability of the resulting compressed solid dispersion may exhibit a hardness from about 15 kP to about 50 kP when a compression force of about 13 kN to about 35 kN is applied. In one embodiment, the compactability of the resulting compressed solid dispersion may exhibit a hardness from about 15 kP to about 35 kP when a compression force of about 13 kN to about 35 kN is applied. In one embodiment, the compactability of the resulting compressed solid dispersion may exhibit a hardness from about 22 kP to about 50 kP when a compression force of about 13 kN to about 35 kN is applied. In one embodiment, the compactability of the resulting compressed solid dispersion may exhibit a hardness greater than 15 kP at a compression force of 13 kN. In one embodiment, the compactability of the resulting compressed solid dispersion may exhibit a hardness greater than 35 kP at a compression force of 35 kN.

In one embodiment, the durability of the resulting compressed solid dispersion may exhibit a friability of 0.5% or less when a compression force of about 13 kN to about 35 kN is applied.

In one embodiment, solid dispersions of the present invention include at least two carbohydrates with different solubilities, wherein the solid dispersion has a microcrystalline plate structure. In one embodiment, solid dispersions of the present invention include at least two carbohydrates with different concentrations, wherein the solid dispersion has a microcrystalline plate structure.

In one embodiment, the crystalline layers of the microcrystalline plate structure have a thickness of less than 5 microns, preferably less than 3 microns and most preferably less than 1 micron. In one embodiment, the crystalline layers of the microcrystalline plate structure have a thickness of about 0.5 microns to about 5 microns. In one embodiment, the crystalline layers of the microcrystalline plate structure have a thickness of about 0.5 microns to about 2 microns. In one embodiment, the crystalline layers of the microcrystalline plate structure are in contact with one another. In some embodiments, the small size of the crystalline layers adds to a creamy mouth feel upon disintegration.

In one embodiment a solid dispersion with a microcrystalline plate structure is achieved by selecting carbohydrates with different solubilities and making a solution within a range of percent of saturation of the different carbohydrate components at a given solution process temperature. Percent of saturation is defined as (component concentrations at process temperature)/(saturation of the component at the process temperature)*100. Temperatures ranging from 40° C. to 99° C. can be used for the solution process temperature. The sequence of co-crystallization that forms the microcrystalline plate structure is predicated on % of saturation of the components in the solution.

In one embodiment, the core carbohydrate component is processed at about 60% to about 99.5% of its saturation concentration, any transition component(s) added at less than about 1% to about 59.5%, and the surface component added at less than about 0.5% to about 40%.

In a more preferred embodiment, the core carbohydrate component is processed at about 75% to about 99.5% of its saturation concentration, any transition component(s) added at less than about 1% to about 24.5%, and the surface component added at less than about 0.5% to about 25%.

In an even more preferred embodiment, the core carbohydrate component is processed at about 85% to about 99.5% of its saturation concentration, any transition component(s) is added at less than about 1% to about 14.5%, and the surface component is added at greater than about 0.5% to about 15%.

In a most preferred embodiment, the core carbohydrate component is processed at about 95% to about 99.5% of its saturation concentration, any transition component is added at greater than about 1% to about 4.5%, and the surface component is added at greater than about 0.5% to about 5%.

While not wishing to be bound by theory, it is speculated that interaction between the co-processed carbohydrates may be substantially responsible for the surprising characteristics of the solid dispersions of some embodiments of the invention.

In one embodiment, a solid dispersion of the present invention comprises three zones: a core, a transition and a surface. Zone one is a first carbohydrate crystal core. Zone two, the transition layer, can be one or multiple layers in which a single dispersed material or multiple dispersed materials are co-crystallized with first carbohydrate. The transition dispersed material serves to segment and plasticize the transition zone. There are two factors that affect the transition; one is the solubility of the dispersed phase in water at the process temperature. (See Table 1 for solubility of various carbohydrates.) The lower soluble dispersed material at the same temperature will co-crystallize later than higher soluble materials. The other factor is the concentration of the dispersed material in solution. The higher the concentration the earlier in the process it will co-crystallize. Thus core thickness and transition zone thickness can be adjusted to get co-crystallization and a thinner core early in process and by adjusting either the solubility of the dispersed material or lowering the concentration-of the dispersed material. Zone three, the surface zone, incorporates carbohydrates for surface placement. The surface is created as a composition of multiple carbohydrates with a reducing surface bonding energy.

TABLE 1

Carbohydrate Solubilities

| Raw Material | Mole Wt | Melt Point ° C. | Solubility At 25 (g/100 g $H_2O$) |
| --- | --- | --- | --- |
| Sorbitol | 182 | 99-101 | 235 g |
| Mannitol | 182 | 165-169 | 22 g |
| HSH | HP+ | N/a | Soluble |
| Maltitol Solution | | N/a | Soluble |
| Maltitol | 344 | 144-147 | 175 g |
| Xylitol | 152.17 | 92-95 | 200 g |
| Lactitol Monohydrate | 362.33 | 95-101 | 140 g |
| Anhydrous Isomalt | 344.32 | 145-150 | 39 g |
| Erythritol | 122 | 119-123 | 61 g |
| Glycerin | 99 | 17.8 | Soluble |
| Polydextrose | <22,000 | 130 | 80 g |
| Sucrose | 342 | 160-186 | 185 g |
| Fructose | 180 | 102-105 | 400 g |
| Maltose | 342 | 120-125 | 70 g |

The use of differential solubility (Percent of saturation) as a means of controlling the microcrystalline plate structure is based on the amount of water remaining in the solid dispersion droplet. Percent of saturation of the first carbohydrate is closest to 100% causing it to crystallize first. As evaporation process continues, the amount of water remaining is lowered to saturation conditions for the next percent of saturation dispersant. Thus co-crystallization occurs of each of the remaining dispersed materials in a planned order. Both cooling and evaporation can cause crystallization. As the process can be setup to be isothermal in a narrow range, the cooling of the particles especially in spray drying is considered negligible. In the following example in Table 2, the solution temperature is 80° C. and the exiting dried product from the spray drier is 85 to 95° C. The droplet cooling is thus limited.

The calculation for evaporation involves calculation of the amount of water remaining to maintain solubility of each material as the process of evaporation continues. Table 2 below shows the solubility at 80° C., the spray liquid temperature. By subtraction from 100, the amount of water needed to be at saturation is calculated in column 2. The selected concentrations of materials are placed into water in this case, 55 kilos of water. Note mannitol crystallizes after 8.84% of the water has evaporated, followed by maltitol co-crystallizing with mannitol at 99.65% water evaporated or 0.35% water remaining and then by sorbitol co-crystallizing at 99.83% evaporated or 0.17% of water remaining. The calculation uses a ratio of (amount of water at saturation)/ (amount of carbohydrate at saturation) as a ratio multiplied by the amount of carbohydrate in batch to determine the amount of water at saturation. For example, (8/92*1.08)=0.0.09375 for sorbitol. The sequence of saturation and the amount of material coming out of solution thus is the determining factor for core, transition and surface composition thickness and composition. Materials selected for inclusion are selected as those that will form a solid dispersion as defined herein.

First crystallization can be a crystalline or co-crystallization material as a core and the transition to the surface can be the same co-crystallization and thus a two carbohydrate system. First, to crystallize, the dispersant phase can be from about 0.5% to about 99.5% of the total mass with a 0% to 99.5% transition zone and 0.5 to 99.5% surface zone.

A solution of three or more carbohydrates with different solubilities is prepared. In order to co-crystallize the carbohydrates into a solid dispersion with a microplate structure, this solution is first processed to approximately 100 percent saturation or more of the carbohydrate with the highest percent saturation in the solution.

The sequence of crystallization/co-crystallization of three or more carbohydrates occurs due to either solvent loss, temperature change of the solution or both. The microplate structure is dictated by the % saturation of carbohydrates selected in preparing the liquid solution to be processed. The process of co-crystallization can be accomplished by spraying the close to ~100% saturation liquid into a fluid bed or spray drier or spraying a nucleated suspension (containing small microcrystals) into a fluid bed or spray drier. Process temperature can be designed for conditions to dry at 40° C. to 210° C. inlet temperatures.

system includes a coated sugar and/or coated sugar mixture. In some embodiments, a solid dispersion is coated.

Components

In some embodiments, a solid dispersion and/or excipient system includes a coated polyol, such as mannitol, or coated polyol mixture. In some embodiments, mannitol may be prepared by spray drying, such as Mannogem™ EZ (SPI Pharma, Inc., Wilmington, Del.) spray dried mannitol. In some embodiments, spray dried mannitol is prepared with a spray drier such as the Buchi Mini-Spray Drier, Model B290. In one embodiment, spray dried mannitol is prepared on the Buchi Model B290 using a 0.7 mm nozzle tip, 200° C. inlet temperature, 90-97° C. outlet temperature maintained by spray rate, an air flow of 15 mL/min, and a 45% mannitol solution at an 80° C. minimum temperature. Mannitol may also be prepared by other suitable methods. Carbohydrates and carbohydrate mixtures such as polyols and polyol mixtures may be prepared by any suitable method, such as, spray drying, fluid bed, co-granulation or high shear mixing as described in the Carbohydrate Mixture sections above.

In some embodiments, suitable coatings may include, but are not limited to, soluble polymer materials. Suitable coatings may include, but are not limited to, polyvinylpyrrolidones, polyvinylalcohols, polyethylene graft copolymers, polyethylene glycols, ethylene glycol/propylene glycol graft coplomers, hydroxypropylmethylcellulose, hydroxypropylcelluose, hydroxyethylcellulose, carrageenans, pectins, xantans and alginates. In some embodiments, a suitable coating includes 60:40 copolymer of vinylpyrrolidone and vinyl acetate (i.e., copovidone) such as Plasdone® S630 (International Specialty Products). In some embodiments, a solid dispersion and/or excipient system includes a coating in an amount of about 0.1 wt % to about 5 wt %; about 0.2 wt % to about 4 wt %; about 0.3 wt % to about 3 wt %; about 0.4 wt % to about 2 wt %; or about 0.5 wt % to about 1 wt %. In some embodiments, a solid dispersion and/or excipient system includes a coating in amount of about 0.1 wt %; about 0.2 wt %; about 0.3 wt %; about 0.4 wt %; about 0.5 wt %; about 0.6 wt %; about 0.7 wt %; about 0.8 wt %; about 0.9 wt %; about 1 wt %; about 1.1 wt %; about 1.2 wt %; about 1.3 wt %; about 1.4 wt %; about 1.5 wt %; about 1.6 wt %; about 1.7 wt %; about 1.8 wt %; about 1.9 wt %; about 2 wt %; about 3 wt %; about 4 wt %; or about 5 wt %.

Methods of Making

Any suitable method may be used to prepare a coated carbohydrate and/or coated carbohydrate mixture.

TABLE 2

Carbohydrate Saturations

| | 80° C. Solubility Kilos/100 Kilo solution | Kilos of water at saturation | % in Formulation | Kilos water at saturation (55 kilos total) | % of water remaining at saturation | % of water dried off at saturation |
|---|---|---|---|---|---|---|
| Sorbitol | 92 | 8 | 1.08 | 0.09375 | 0.17% | 99.83% |
| Maltitol | 80.5 | 19.5 | 0.8 | 0.193032 | 0.35% | 99.65% |
| Mannitol | 47.3 | 52.7 | 45 | 50.13742 | 91.16% | 8.84% |
| Isomalt | 71 | 29.0 | | | | |
| Lactitol | 82 | 18.0 | | | | |

Coated Carbohydrate

In some embodiments, a solid dispersion and/or excipient system includes a coated carbohydrate and/or a coated carbohydrate mixture. In some embodiments, a solid dispersion and/or excipient system includes a coated polyol and/or coated polyol mixture. In some embodiments, an excipient Fluid Bed In some embodiments, a coated carbohydrate, such as a polyol or sugar, or coated carbohydrate mixture, such as a polyol mixture or sugar mixture, is prepared using a fluid bed. In one example, mannitol coated with copovidone can be made as follows:

Ingredient List:

| DESCRIPTION | QTY (kg) | Supplier |
|---|---|---|
| Mannitol (Mannogem EZ USP/EP) | 396.0 | SPI Pharma |
| Copovidone (Plasdone S-630) | 4 | ISP Corp |
| Total | 400 | |

Using, a Fluid Air 1000 fluid bed dryer GRANULATOR, Mannogem EZ is charged into the fluid bed. The product temperature is allowed to reach at least 30° C. prior to spraying the solution. The solution is 4 kg of S-630 in 29 kg of water, and is made by adding the Plasdone S-630 slowly to a stirring of the solution.

The spraying process parameters include 2000-4000 SCFM (target: 2800 SCFM), inlet air temperature of 75-100° C., and a solution spray rate of 0.5-2.0 kg/min. The approximate operating time is 30 minutes of spraying. Once the spraying of the solution is complete, the batch may be dried according to the following parameters: product temperature of 30-40° C. (target 35° C.) and air flow of 1000-3000 SCFM. When the outlet temperature reaches approximately 35° C., a sample may be pulled and tested for moisture via a standard lod test. If the target moisture level of less than or equal to 1.0% is not reached, the batch may be cooled.

High Shear

In some embodiments, a coated carbohydrate, such as a polyol or sugar, or coated carbohydrate mixture, such as a polyol mixture or sugar mixture, is prepared using high shear. In one example, mannitol coated with copovidone is prepared by first adding 20 kg of mannitol (such as Mannogem EZ) and 60 g of Plasdone S-630 (PVNA copolymer) using a high shear mixer, such as Littleford Lodige 5 cu ft high shear granulator (JH DAY, Cincinnati, Ohio). A solution is made of 12% Plasdone S-630 in water using 140 g copovidone and 210 g of mannitol per 1173 mL of water. With the mixer ploughs running at 60 RPM, the copovidone solution is slowly sprayed. The product can then be dried in a fluid bed, such as Fluid Air Model 50 L (Fluid Air Corp, Aurora, Ill.), at an inlet temperature of 60° C. and air flow of 150 SCFM until the product contains less than 0.5% moisture.

Characteristics

In some embodiments, a solid dispersion and/or excipient system including a coated carbohydrate, such as a polyol or sugar, or coated carbohydrate mixture, such as a polyol mixture or sugar mixture, exhibits superior functionality such as tabletability, organoleptic characteristics, and faster disintegration times. Excipient systems including a coated carbohydrate, such as a polyol or sugar, or coated carbohydrate mixture, such as a polyol mixture or sugar mixture, may rapidly develop a thin smooth liquid suspension in the mouth on disintegration (creamy mouth feel) at about 1% or less concentration of water soluble polymer without effecting the overall disintegration time of the tablet made from this composition. In some embodiments, in orally disintegrating tablets, the creamy mouth feel suspension developed helps hide large particle APIs, and reduces an unpleasant feeling of grittiness as suspension particles are thin microplates and dissolvable. In some embodiments, an excipient system including a coated carbohydrate, such as a polyol or sugar, or coated carbohydrate mixture, such as a polyol mixture or sugar mixture, exhibits low friability even at the lower compression forces.

Combination Excipient System

In some embodiments, an excipient system includes (1) a solid dispersion of at least two carbohydrates and (2) a coated carbohydrate or carbohydrate mixture. In some embodiments, an excipient system includes (1) a solid dispersion of at least three carbohydrates and (2) a coated carbohydrate and/or coated carbohydrate mixture.

Components

In some embodiments, an excipient system includes a mixture of at least two carbohydrates, such as polyols and/or sugars. A suitable carbohydrate mixture may include, for example, mannitol and maltitol. In some embodiments, an excipient system includes a mixture of at least three carbohydrates, such as polyols and/or sugars. A suitable carbohydrate mixture may include, for example, mannitol, maltitol, and sorbitol. The carbohydrates may be co-spray dried or co-granulated, as described above. In some embodiments, an excipient system includes mannitol and maltitol in the relative amounts described above. In some embodiments, an excipient system includes about 30 wt % to about 70 wt % polyol mixture; about 40 wt % to about 60 wt % polyol mixture; about 45 wt % to about 55 wt % polyol mixture; about 47 wt % to about 53 wt % polyol mixture; or about 50 wt % polyol mixture.

In some embodiments, an excipient system includes a coated carbohydrate, such as a polyol or sugar, or coated carbohydrate mixture, such as a polyol mixture or sugar mixture, as described above. An excipient system may include about 1 wt % to about 40 wt % coated carbohydrate or carbohydrate mixture; about 5 wt % to about 35 wt % coated carbohydrate or carbohydrate mixture; about 10 wt % to about 30 wt % coated carbohydrate or carbohydrate mixture; about 15 wt % to about 25 wt % coated carbohydrate or carbohydrate mixture; about 17 wt % to about 23 wt % coated carbohydrate or carbohydrate mixture; or about 20 wt % coated carbohydrate or carbohydrate mixture.

Methods of Making

In some embodiments the components described above are admixed. The mixture may then be compressed to tablet form by known methods with or without a coated or uncoated or modified Active Pharmaceutical Ingredient (API).

Characteristics

In some embodiments, an excipient system including a carbohydrate mixture as described herein and a coated carbohydrate or carbohydrate mixture (e.g., at least one spray dried polyol coated with a soluble polymer material), as described above, demonstrates superior functionality such as tabletability, durability, organoleptic characteristics, faster disintegration time, and/or an advantageous decrease in sensitivity to the compaction pressure. For example, in some embodiments, an increased compaction pressure results in a tablet displaying a more favorable friability value, increased hardness values, and surprisingly, only a slight or no increase in disintegration time.

Additionally, lower compaction pressures may be required to achieve a tablet with acceptable hardness and friability values. In some embodiments, an excipient system including a coated carbohydrate or carbohydrate mixture and a carbohydrate mixture exhibits low friability even at the lower compression forces. These properties may be useful for maintaining taste-masking or controlled release properties of APIs during compaction by avoiding rupture of such components as the taste mask coating or a modified active. In some embodiments, actives are modified to decrease unpleasant taste, control its release, increase bioavailability by improving solubility and/or permeation, or to stabilize the API. In some embodiments, such modifications prevent rupture of the bioenhancement coating or fracture of the bioenhanced API structure. Being able to form tablets at lower forces may allow for this structure to remain more intact during the tablet process and may deliver the API more effectively to the patient. Increased compactability at lower compression forces also reduces tablet press and punch wear.

In some embodiments, an excipient system including a carbohydrate mixture and a coated carbohydrate or carbohydrate mixture exhibits superior functionality such as organoleptic characteristics. Excipient systems including a carbohydrate mixture and a coated carbohydrate or carbohydrate mixture may rapidly develop a thick, smooth liquid in the mouth on disintegration (creamy mouth feel) at about 1% or less concentration of water soluble polymer without effecting the overall disintegration time of the tablet. In some embodiments, such superior organoleptic functionality helps hide large particle coated or uncoated APIs, and reduces the feeling of grittiness.

In some embodiments, an excipient system including a carbohydrate mixture and a coated carbohydrate or carbohydrate mixture exhibits superior dilution potential. In some embodiments, an excipient system including a carbohydrate mixture and a coated carbohydrate or carbohydrate mixture retains its functionality even after dilution with another material such as an API or disintegrant. In some embodiments, an excipient system may be highly compactable, accommodating a high dose of API and thereby facilitating creation of a more robust tablet. In some embodiments, an excipient system including a carbohydrate mixture and a coated carbohydrate or carbohydrate mixture is highly compactable, as application of a low compression force results in a tablet with moderate to high hardness levels.

Additional Components for Excipient Systems

The excipient systems listed above may include a number of additional components.

In some embodiments, an excipient system includes a polyol. A suitable polyol may include mannitol, such as Mannogem™ EZ (SPI Pharma, Inc., Wilmington, Del.) spray dried mannitol. In some embodiments, an excipient system includes about 1 wt % to about 30 wt % polyol; about 5 wt % to about 25 wt % polyol, about 10 wt % to about 20 wt % polyol; about 12 wt % to about 18 wt % polyol; or about 15 wt % polyol.

In some embodiments, an excipient system includes a disintegrant. Suitable disintegrants include but are not limited to crospovidone (e.g. Plasdone® XL, Kollidone®, Polyplasdone®), alginic acid, croscarmellose sodium (e.g. Ac-Di-Sol®, Primellose®), guar gum, microcrystalline cellulose, polacrilin potassium, powdered cellulose, sodium alginate, and sodium starch glycolate (e.g. Explotab®). In some embodiments, an excipient system includes about 1 wt % to about 30 wt % disintegrant; about 5 wt % to about 25 wt % disintegrant; about 10 wt % to about 20 wt % disintegrant; about 12 wt % to about 18 wt % disintegrant; or about 15 wt % disintegrant.

Additional suitable components may also be included in an excipient system of the present invention at amounts appropriate to achieve the desired properties.

In some embodiments, an excipient system includes a mixture of at least two carbohydrates and a disintegrant. In some embodiments, an excipient system includes a mixture of at least two polyols, such as mannitol and maltitol, and a disintegrant. In some embodiments, an excipient system includes a mixture at least three carbohydrates and a disintegrant. In some embodiments, an excipient system includes a mixture at least three polyols, such as mannitol, maltitol, and sorbitol, and a disintegrant.

In some embodiments, an excipient system includes a mixture at least two carbohydrates, a disintegrant, and a carbohydrate. In some embodiments, an excipient system includes a mixture at least two polyols, such as mannitol and maltitol, a disintegrant, and a polyol. In some embodiments, an excipient system includes a mixture of at least three carbohydrates, a disintegrant, and a carbohydrate. In some embodiments, an excipient system includes a mixture of at least three polyols, such as mannitol, maltitol, and sorbitol, a disintegrant, and a polyol.

In some embodiments, an excipient system includes a mixture at least two carbohydrates, a disintegrant, and a coated carbohydrate. In some embodiments, an excipient system includes a mixture at least two polyols, such as mannitol and maltitol, a disintegrant, and a coated polyol. In some embodiments, an excipient system includes a mixture of at least three carbohydrates, a disintegrant, and a coated carbohydrate. In some embodiments, an excipient system includes a mixture of at least three polyols, such as mannitol, maltitol, and sorbitol, a disintegrant, and a coated polyol.

In some embodiments, an excipient system includes a mixture at least two carbohydrates, a disintegrant, a carbohydrate, and a coated carbohydrate. In some embodiments, an excipient system includes a mixture at least two polyols, such as mannitol and maltitol, a disintegrant, a polyol, and a coated polyol. In some embodiments, an excipient system includes a mixture of at least three carbohydrates, a disintegrant, a carbohydrate, and a coated carbohydrate. In some embodiments, an excipient system includes a mixture of at least three polyols, such as mannitol, maltitol, and sorbitol, a disintegrant, a polyol, and a coated polyol.

In some embodiments, an excipient system includes a coated carbohydrate and a disintegrant. In some embodiments, an excipient system includes a coated polyol and a disintegrant. In some embodiments, an excipient system includes a coated carbohydrate, a carbohydrate, and a disintegrant. In some embodiments, an excipient system includes a coated polyol, a polyol, and a disintegrant. In some embodiments, an excipient system includes a carbohydrate and a disintegrant. In some embodiments, an excipient system includes a polyol and a disintegrant.

In some embodiments, an excipient system includes a glidant. Suitable glidants include but are not limited to silica gel, colloidal silica, fumed silica, precipitated silica, talc, and mixtures thereof. The glidant component of the co-processed carbohydrate system preferably is present in a range of from about 0% to about 5% of the total weight of the system.

The silica gel acts to improve the flow properties of the composition and minimize the amount of material that sticks to the punches and dies during tableting. The colloidal silica acts to improve the flow properties of the composition before it is tableted.

Formulation

In some embodiments, a pharmaceutical formulation includes an excipient system as described above. In some embodiments, a pharmaceutical formulation includes a suitable amount of excipient system. In some embodiments, a pharmaceutical formulation includes about 20 wt % to about 99 wt % excipient system. In some embodiments, a pharmaceutical formulation includes about 20 wt % to about 95 wt % excipient system; about 25 wt % to about 90 wt % excipient system; about 25 wt % to about 85 wt % excipient system; about 25 wt % to about 80 wt % excipient system; about 25 wt % to about 75 wt % excipient system; about 25 wt % to about 75 wt % excipient system; about 30 wt % to about 70 wt % excipient system; about 35 wt % to about 65 wt % excipient system; about 40 wt % to about 60 wt % excipient system; about 45 wt % to about 55 wt % excipient system; or about 50 wt % excipient system.

In some embodiments, a pharmaceutical formulation includes an API. Suitable such APIs include but are not limited to those described in the *Physician's Desk Reference*, 61st ed. Montvale, N.J.: Thomson PDR; 2007, which is incorporated by reference herein in its entirety. In some embodiments, a pharmaceutical formulation includes about 1 wt % to about 75 wt % API; about 5 wt % to about 70 wt %; about 10 wt % to about 65 wt %; about 15 wt % to about 60 wt %; about 25 wt % to about 55 wt % API; about 30 wt % to about 50 wt % API; about 35 wt % to about 45 wt % API; about 37 wt % to about 43 wt % API; or about 40 wt % API.

In some embodiments, a pharmaceutical formulation includes suitable components including but not limited to lubricants, flavors, sweeteners, and colors, in amounts appropriate to achieve the desired properties.

Solid Dosage Forms

In one embodiment of the present invention, the solid dispersion formulation is directly compressed into a solid dosage form (e.g., a tablet) using a standard compression equipment (e.g., a tableting press). One embodiment of the directly compressed solid dosage form of the present invention dissolves or disintegrates within 10 minutes, preferably within less than 6 minutes. One embodiment of the directly compressed solid dosage form of the present invention disintegrates within the stomach or intestine within 10 minutes, preferably within less than 6 minutes.

In one embodiment of the present invention, the solid dispersion formulation is directly compressed into a swallow tablet or lozenge using standard compression equipment (e.g., a tableting press). One embodiment of the swallow tablet or lozenge of the present invention dissolves or disintegrates within 10 minutes, preferably within less than 6 minutes. One embodiment of the swallow tablet or lozenge of the present invention disintegrates within the stomach or intestine within 10 minutes, preferably within less than 6 minutes.

In one embodiment of the present invention, the solid dispersion formulation is directly compressed into a solid dosage form (e.g., a tablet) using a standard compression equipment (e.g., a tableting press). One embodiment of the directly compressed solid dosage form of the present invention interacts with saliva in the oral cavity of a patient and completely dissolves or disintegrates in the oral cavity into an easily swallowable form within about 60 seconds.

In one embodiment of the present invention, the solid dispersion formulation is directly compressed into an orally dispersible tablet using standard compression equipment (e.g., a tableting press). One embodiment of the orally dispersible tablet of the present invention completely dissolves or disintegrates in the oral cavity within about 60 seconds.

In one embodiment of the present invention, the solid dispersion formulation is directly compressed into a chewable tablet using standard compression equipment (e.g., a tableting press). One embodiment of the chewable tablet of the present invention completely dissolves or disintegrates in the oral cavity into within about 60 seconds.

In an embodiment of the invention, the solid dosage form completely dissolves or disintegrates within about 25 to 50 seconds after placing the tablet in the oral cavity. In an embodiment of the invention, the solid dosage form completely dissolves or disintegrates within about 5 to 20 seconds after placing the tablet in the oral cavity. In one embodiment of the present invention, the solid dosage form completely dissolves or disintegrates in the oral cavity in less than 60 seconds. In one embodiment of the present invention, the solid dosage form completely dissolves or disintegrates in the oral cavity in less than 50 seconds. In one embodiment of the present invention, the solid dosage form completely dissolves or disintegrates in the oral cavity in less than 40 seconds. In one embodiment of the present invention, the solid dosage form completely dissolves or disintegrates in the oral cavity in less than 30 seconds. In one embodiment of the present invention, the solid dosage form completely dissolves or disintegrates in the oral cavity in less than 20 seconds. In one embodiment of the present invention, the solid dosage form completely dissolves or disintegrates in the oral cavity in less than 10 seconds. In one embodiment of the present invention, the solid dosage form completely dissolves or disintegrates in the oral cavity in less than 5 seconds.

In one embodiment, the solid dosage forms produced in the present invention preferably have a hardness (standard USP method) in the range of about 1 kP to about 50 kP and a friability (standard USP method) in the range of about 0.01% to about 5%.

In one embodiment of the present invention, the solid dosage forms produced have a hardness from about 7 to about 39.9 kP and a friability of less than about 0.5% and a disintegration of less than about 30 seconds.

In one embodiment of the present invention, the solid dosage forms produced have a hardness range of about 4.8 kP to about 34.1 kP and a friability of less than about 0.2% and a USP disintegration of less than about 60 seconds.

In one embodiment of the present invention, the solid dosage forms produced have a hardness (standard USP method) in the range of about 3 kP to about 15 kP and a friability (standard USP method) in the range of about 0.01% to about 2%, and would dissolve or disintegrate in less than 60 seconds.

In some embodiments, a solid dosage form includes a solid dispersion with a mixture of at least two carbohydrates. In some embodiments, a solid dosage form includes a solid dispersion with a mixture of at least two polyols. In some embodiments, a solid dosage form includes a solid dispersion with a mixture of at least two sugars. In some embodiments, a solid dosage form includes a solid dispersion with a mixture of at least three carbohydrates. In some embodiments, a solid dosage form includes a solid dispersion with a mixture of at least three polyols. In some embodiments, a solid dosage form includes a solid dispersion with a mixture of at least three sugars. Carbohydrates, including but not limited to polyols and sugars, suitable for the solid dispersions of the present invention are described above. In some embodiments, a solid dosage form of the present invention includes a solid dispersion including mannitol and maltitol. In some embodiments, a solid dosage form of the present invention includes a solid dispersion including mannitol and isomalt. In some embodiments, a solid dosage form of the present invention includes a solid dispersion including mannitol, maltitol, and sorbitol. In some embodiments, a solid dosage form of the present invention includes a solid dispersion including mannitol, isomalt, and sorbitol.

In some embodiments, a solid dosage form of the present invention includes a solid dispersion including mannitol, maltitol, and sorbitol. In some embodiments, a solid dosage form of the present invention includes a solid dispersion including mannitol, lactitol, and sorbitol. In some embodiments, a solid dosage form of the present invention does not include xylitol.

The highly compactable solid dispersions and excipient systems of the present invention may be used as a delivery platform for one or more active ingredients. One or more active ingredients may be mixed with the solid dispersion and formed into a solid dosage form, such as a tablet. In another embodiment, additional ingredients such as a lubricant, flavor, color, or sweetening agent may also be added to the formulation and formed into a solid dosage form.

When the solid dosage form is placed in the oral cavity of a patient, it interacts with saliva and rapidly dissolves or disperses in the oral cavity of the patient. As the solid dosage form dissolves in the oral cavity of the patient, it releases the one or more active ingredients contained in the solid dosage form.

It will be apparent to one of skill in the art that various modifications and variations can be made in the methods and compositions of the present invention without departing from the spirit or scope of the invention. Thus, it is intended that the present invention cover the modifications and variations of the present invention provided they come within the scope of the appended claims and their equivalents.

The following examples are given to illustrate the present invention. It should be understood, however, that the invention is not to be limited to the specific conditions or details described in these examples. Throughout the specification, any and all referenced publicly available documents, including but not limited to a U.S. patent, are specifically incorporated by reference.

EXAMPLES

Example 1

Solid Dispersion of Three Co-Processed Carbohydrates with Microcrystalline Plate Structure Water is charged to an agitated jacketed mix tank, and the water heated to 78-90° C. The following raw materials are added to the mix tank with agitation.

| Material | Amount in Kilos | Percent of Saturation |
|---|---|---|
| Mannitol | 600 kilos | |
| Maltitol | 10.6 | |
| Sorbitol | 14.4 | |
| Purified Water | 760 kilos | |
| Silicon dioxide | Up to 1% as process aid | |

When the raw materials are in solution and at temperature, the solution is spray dried by the following process.

A 7" rotary atomizer is set-up with a feed pump and the ability to recycle smaller sized particles by fluid bed classification back to the spray drying chamber, as shown in FIG. 1 and described in Methods of Making-Co-Spray Dried section. The spray dryer parameters are as follows: dryer inlet temperature 195-205° C.; fluid bed inlet temperature 74-122° C. (for monitoring purposes only); dryer outlet temperature 80-95° C. (target 89-92° C.); atomizer wheel speed 11250-11600 rpm. The solution is sprayed into a drier outlet air temperature of 85 to 90° C. The product Solid Dispersion A is collected once the system is stabilized and after approximately 25 kilos of product is produced. The moisture content of the discharged product should be less than 0.3%.

Figure 2:
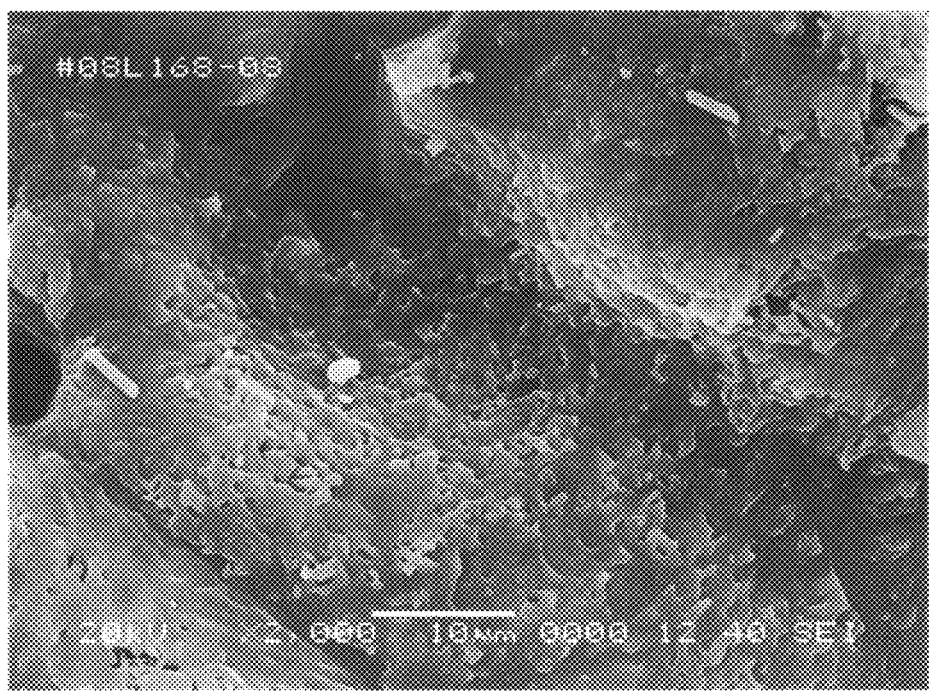
FIG. 2 is a SEM (magnification 2000×) of Solid Dispersion A after co-spray drying.

FIG. 2 is a SEM (magnification 2000×) of solid dispersion Solid Dispersion A demonstrating the microcrystalline plate structure. FIG. 2 clearly shows the plates in the microcrystalline plate structure. In this embodiment, the plates are less than 1 μm in thickness, as compared to the 10 μm scale in FIG. 2, and are arranged in layers. Each layer can be seen as a relatively continuous film. The layers are held together by the attraction of surfaces that are comprised of a eutectic formed from the three polyols. It is believed that the microcrystalline plate structure is due to the difference in solubilities and concentrations of the polyols.

Maltitol has the following chemical structure, with one glucose ring and one sorbitol moiety attached:

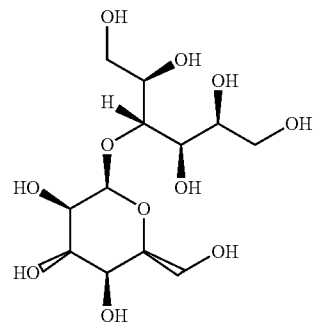 [SMILES: OC[C@@H](O)[C@@H](O[C@H]1O[C@@H](CO)[C@@H](O)[C@@H](O)[C@H]1O)[C@H](O)[C@@H](O)CO]

Notably, three of the five hydroxyls on attached sorbitol are facing up in the sorbitol structure giving the attached sorbitol a highly polar area facing up. Also based on the 1,4 linkage the sorbitol moiety is held at an angle to the glucose ring.

At 80 C in solution Mannitol has a solubility of about 47.% in water, maltitol has a solubility of about 80% in water, and sorbitol has a solubility of about 92% in water In the drying process, based on solubility and concentration used, mannitol will crystallize from solution first, and very early. The mannitol will form nuclei and also grow formed nuclei. Maltitol will begin to co-crystallize with mannitol, followed by the sorbitol component.

The center of the plates is composed of the high melting (thus high bond strength) mannitol that crystallizes first and throughout the drying process based on its close to saturation concentration in the solution being dried. The entire particle by differential scanning calorimetry (DSC) is a single peak eutectic mixture with a crystalline core (vs three peaks, one for each of the 3 polyols) called a fusion form as the heat of fusion of mannitol is slightly changed from an expected 293 J/gm to ~280 J/gm but it's single melt point still is a characteristic beta or alpha mannitol melt point of ~166 C. The formation forms a plasticized plate with an eutectic transition, which limits plate thickness and also plate surface tackiness.

Figure 3:
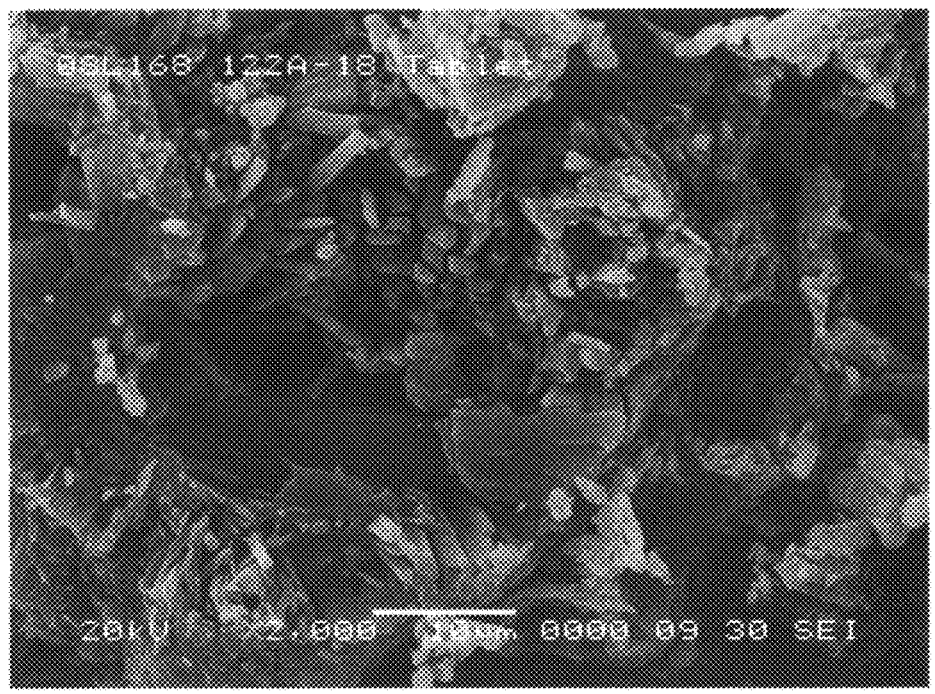
FIG. 3 is a scanning electron micrograph (SEM) (magnification 2000×) of a broken cross section of Solid Dispersion A after compression into tablet.

This eutectic surface generates a bond transition between layers that is weakly bounded, thus allowing low pressure fracturing. The thinness and planar nature of the plates allow for fracture of crystal fragments in the shape of splinters that can be seen in FIG. 3. FIG. 3 is an SEM of the interior structure of a Solid Dispersion A tablet compressed at 20 kN compression pressure broken in half. The width of the broken chips is less than a few microns in size and less than one micron in thickness.

To make the solid dosage form tablet in FIG. 3, Solid Dispersion A was blended in an 8 Quart Vee Mixer (Paterson-Kelley, East Strausburg, Pa.) with 1.5% magnesium stearate for 10 minutes. Tablets were made at a speed of 26 RPM without use of pre-compression. A FFBE (flat-faced beveled edge) 0.625 inch diameter tablet station was used on a Mini-Press (Globe Pharma, New Brunswick, N.J.). The tablet weight was 1.0 gm.

The mannitol crystal 'splinters" is a "moving unit" that is pushed into spaces that are still open in a tablet as pressure is applied. The efficiency of moving to an area of lower pressure from an area of higher pressure gives the advantage of plastic deformation. These splinters move to the tablet outer surface at low pressure and create a more durable, lower friable surface.

Figure 4:
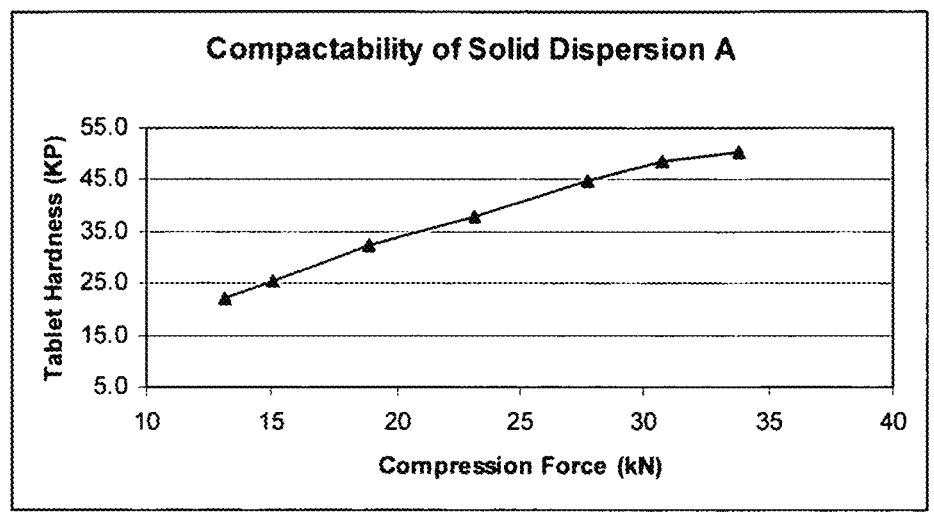
FIG. 4 is a graph depicting hardness as a function of compression force for tableted Solid Dispersion A.
Figure 5:
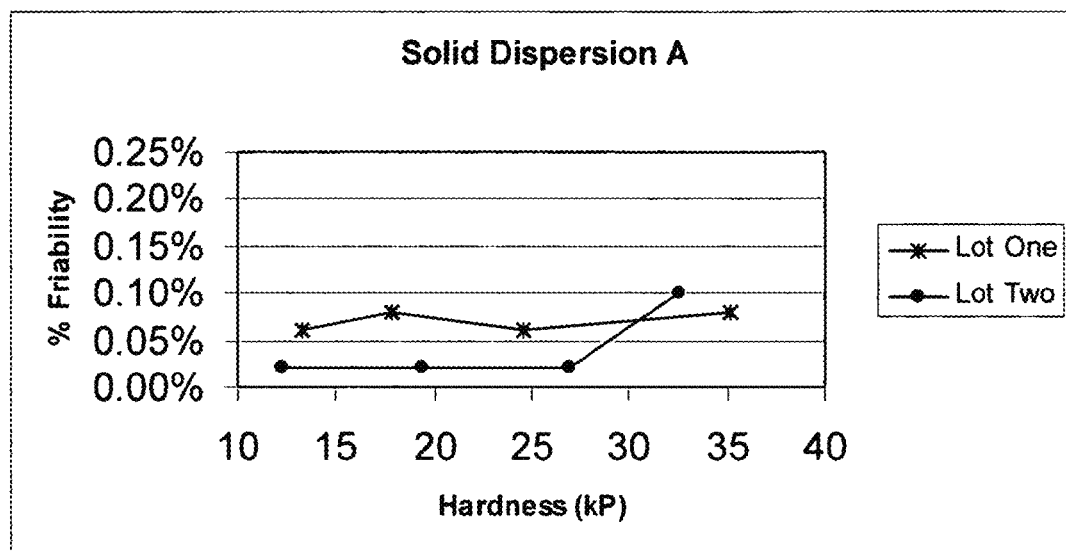
FIG. 5 is a graph depicting friability as a function of hardness for tableted Solid Dispersion A.

As can be seen in FIGS. 4 and 5, it was surprising that at 13 kN compression force a hardness of 22 kP was found and a friability of less than 0.03%. What is even more surprising is the hardness increased linearly from 13 kN compression force applied to 33 kN compression force and was at a maximum of 50 kP hardness at 33 kN compression pressure with the friability remaining below 0.2%, even below 0.15% for the entire compression force range. The same process applied to other compositions may result in lower hardness values. For example, in some embodiments, 97.7 wt % mannitol with 2.3% sorbitol exhibited a hardness of 14 kP at 13 kN, and 90% mannitol with 10% sorbitol, co-spray dried, exhibited a hardness of 16 kP at 13 kN.

The increase in transition phase segmentation and surface orientation is evident in the almost 50 kP hardness generated for the Solid Dispersion A at a pressure of 32 kN versus 32 kP for the 90% mannitol and 10% sorbitol spray dried product at 32 kN. The optimization of layering is seen also in the 6.04% maltitol/2.3% sorbitol product, which exhibited a hardness of 13 kP at a compression force of 13 kN and 44 kP at a compression force of 32 kN.

Table 3 below summarizes the physical characteristics of solid dispersion Solid Dispersion A.

ous magnifications of Mannitol HS. FIGS. 6J-6K show various magnifications of Parteck® M200. FIGS. 7A-7C are SEMs of Solid Dispersion A at various magnifications showing the microcrystalline plate structure.

The SEMs of the above spray-dried materials show crystalline structures that exhibit distinct differences based on the composition and concentrations. The lower percentage of sorbitol (~1%) in Mannogem EZ EP grade results in a primary particle that is a segmented deposit of crystalline fragments. The droplets in the process of drying separates into narrow width crystalline surface fragments. The slightly higher level of sorbitol (~2%) in Mannogem EZ USP grade results in a surface in which as the droplets dry they form a segmented deposit with more rounded edges. It is believed that the more rounded edges and the puckered appearance of the deposit is due to the coalescence of mannitol and sorbitol at its edges. Mannitol HS, which has a much higher level of sorbitol (~12%), has a surface that is more continuous as evidenced by its smooth surface and rounded, merged edges. Droplets of Mannitol HS appear to be coalescing/merging to form a film deposit with the surfaces below with a tightened attachment. This film structure is further demonstrated by the presence of 2 distinct peaks in a DSC scan.

The surface structure of Parteck® M200 (<2% sorbitol) appears to be similar to Mannogem EZ EP grade with segmented deposits of crystalline fragments with some filamentous attachments.

TABLE 3

Characteristics of Tablets made from Solid Dispersion A
Tableted Solid Dispersion A

| Compression Force | | Pressure | Mean Hardness | | STDEV Hardness | Thickness | | Radial Tensile Strength | Density | Friability | USP Dis Time |
|---|---|---|---|---|---|---|---|---|---|---|---|
| Nts | KN | Mpa | kP | N | kP | mm | Sdev | Mpa | g/cm3 | (%) | (sec) |
| 13161 | 13.16 | 67 | 21.8 | 213.3 | 0.472 | 4.516 | 0.0032 | 1.895 | 1.123 | 0.11 | 160 |
| 15032 | 15.03 | 76 | 25.5 | 250.0 | 0.588 | 4.434 | 0.0074 | 2.262 | 1.142 | 0.14 | 180 |
| 18881 | 18.88 | 95 | 32.3 | 316.4 | 0.500 | 4.303 | 0.0036 | 2.949 | 1.177 | 0.15 | 229 |
| 23135 | 23.14 | 117 | 37.9 | 371.1 | 0.670 | 4.181 | 0.0069 | 3.561 | 1.209 | 0.13 | 396 |
| 27761 | 27.76 | 140 | 44.7 | 438.3 | 0.960 | 4.099 | 0.0103 | 4.289 | 1.235 | 0.12 | 534 |
| 30718 | 30.72 | 155 | 48.5 | 475.6 | 1.023 | 4.040 | 0.0057 | 4.721 | 1.250 | 0.13 | 529 |
| 33819 | 33.82 | 171 | 50.3 | 492.5 | 1.33 | 3.998 | 0.01 | 4.942 | 1.266 | 0.130 | 553 |

Example 2

Comparison of Solid Dispersion A with Microcrystalline Plate Structure with Other Excipients and Excipient Systems Solid dispersion Solid Dispersion A, as described in Example 1, is compared to the following excipient systems.

Figure 6A:
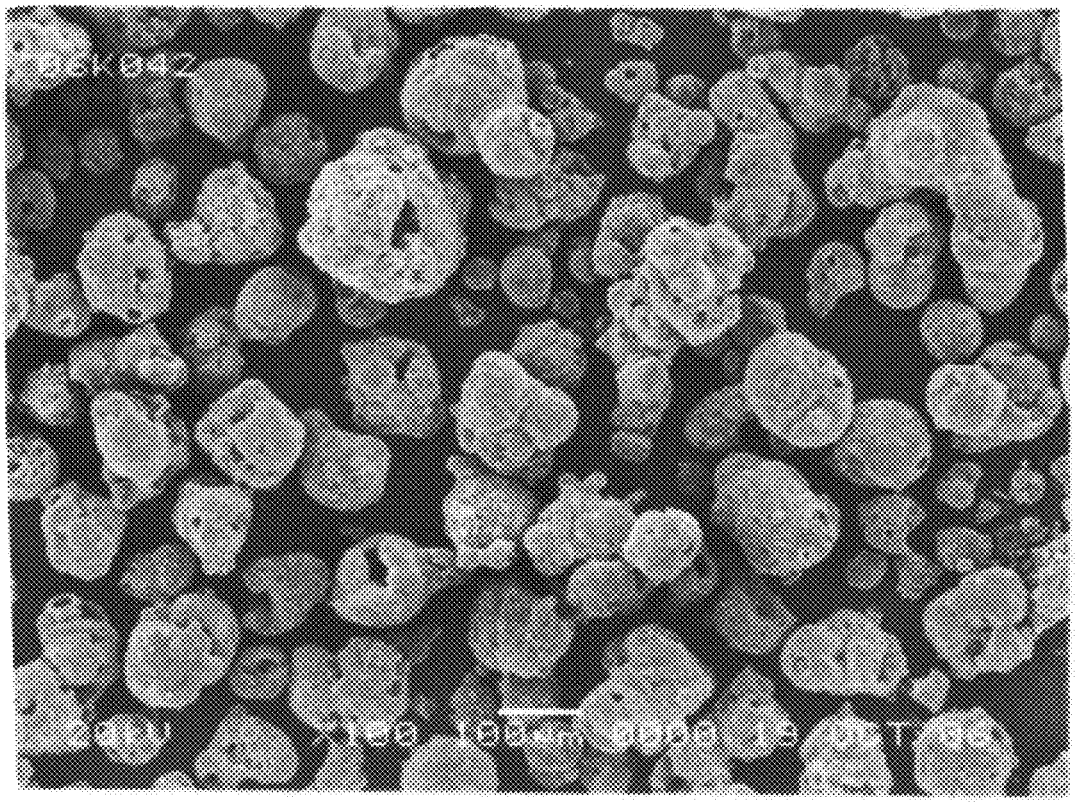
Figure 6B:
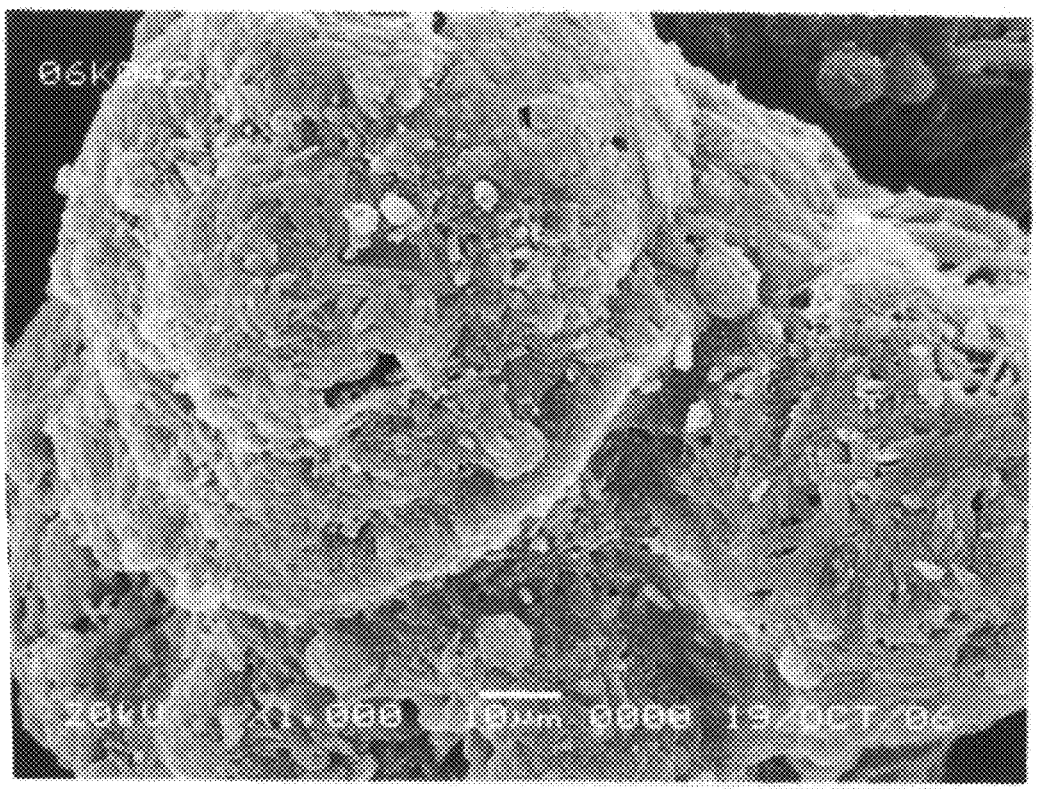
Figure 6C:
Figure 6D:
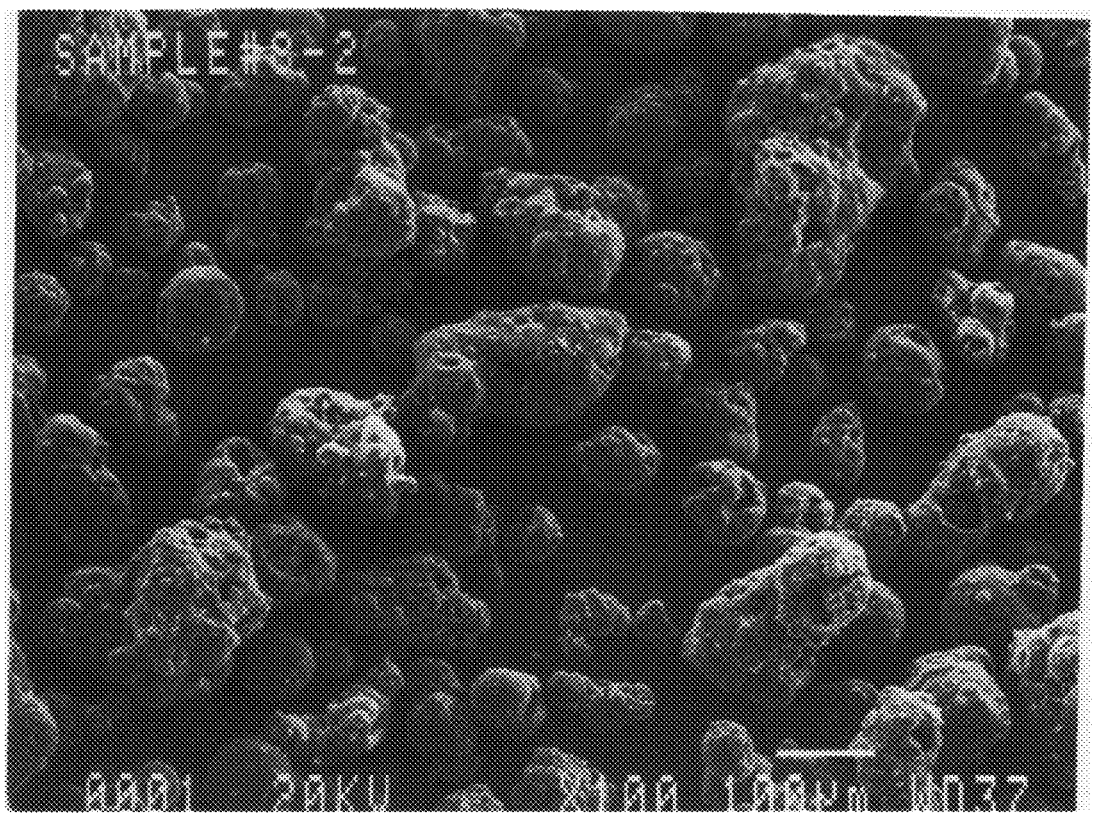
Figure 6E:
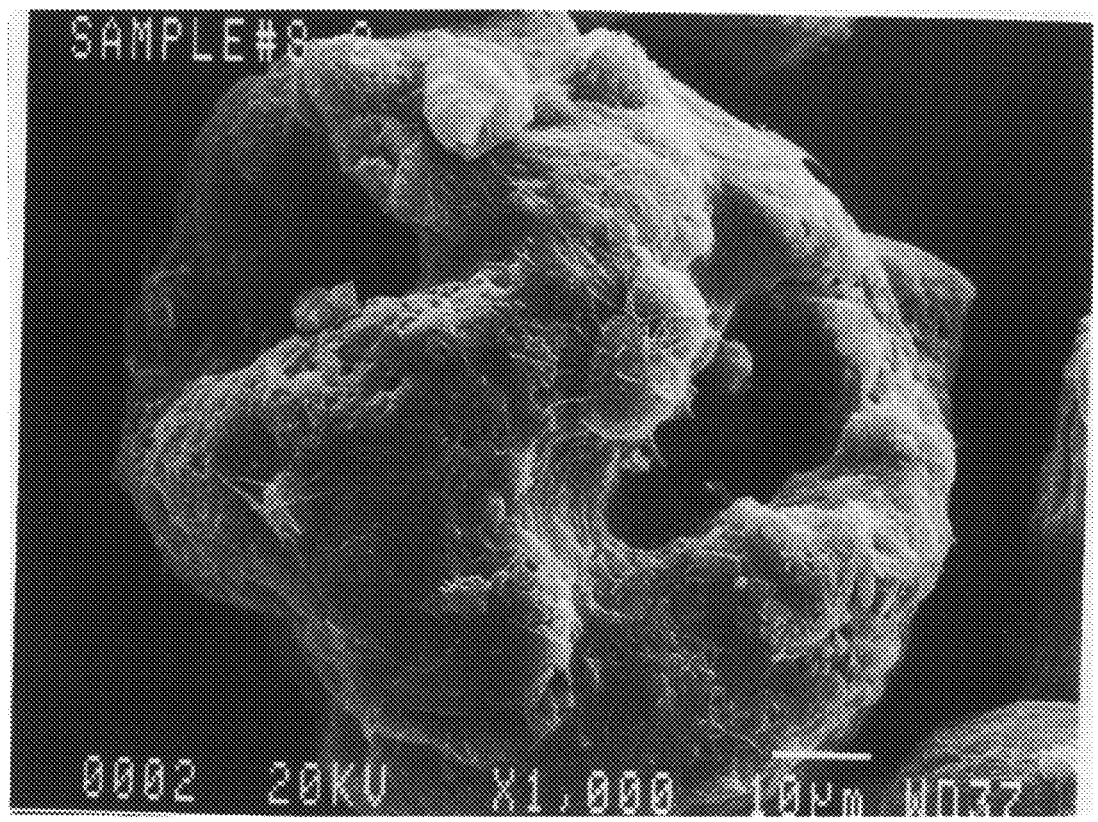
Figure 6F:
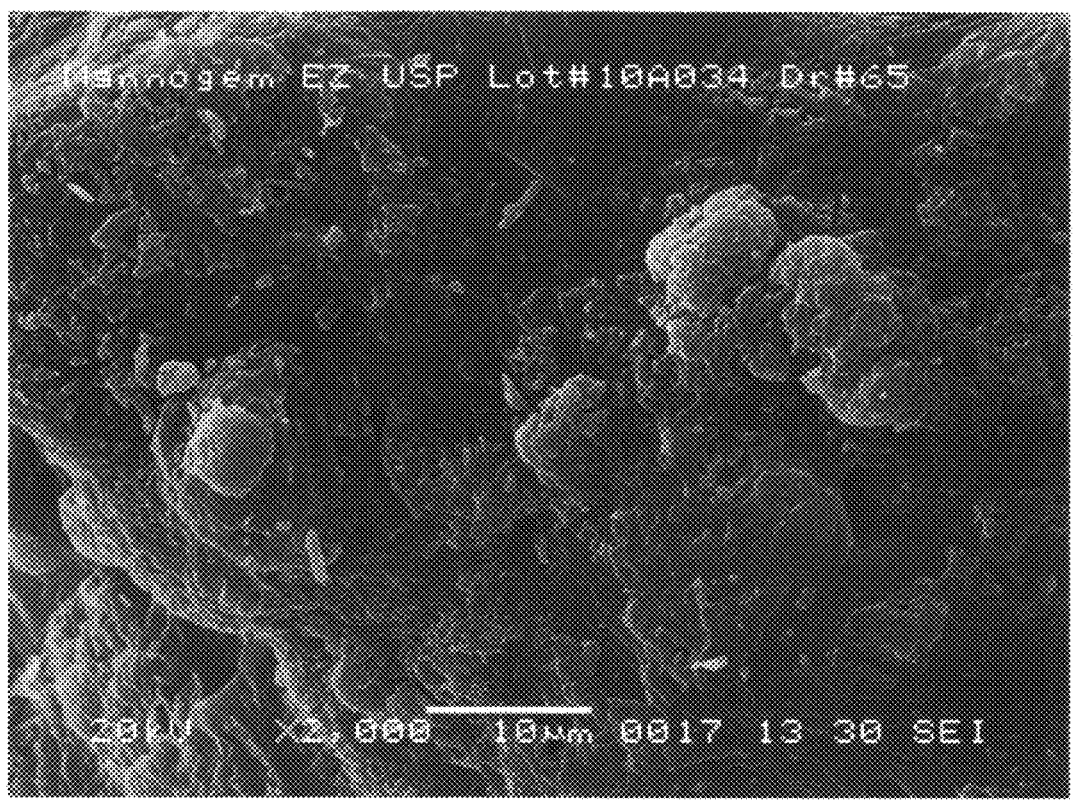
Figure 6G:
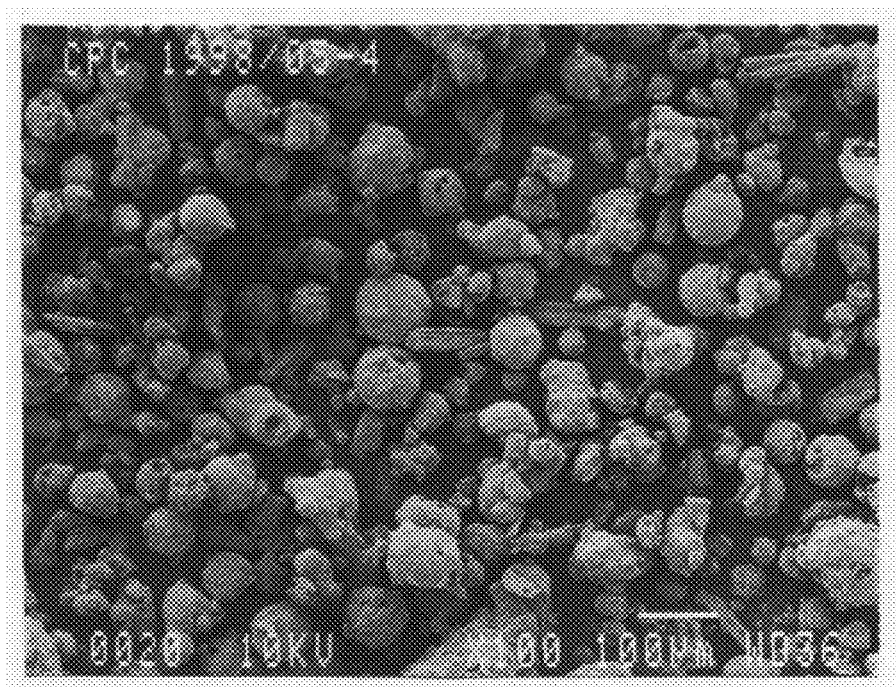
Figure 6H:
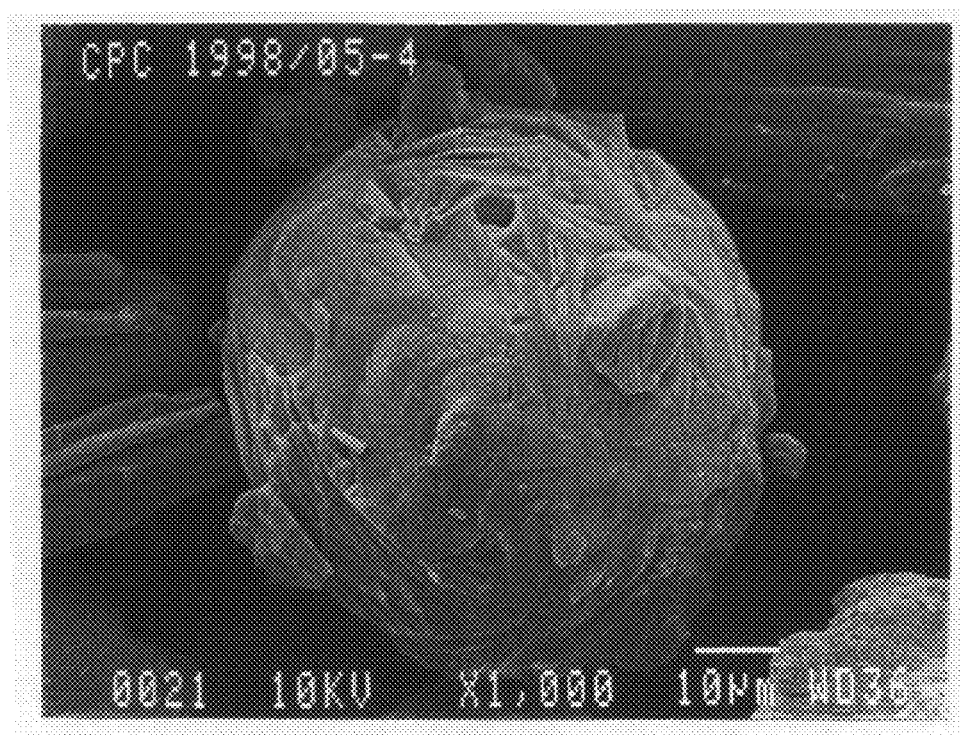
Figure 61:
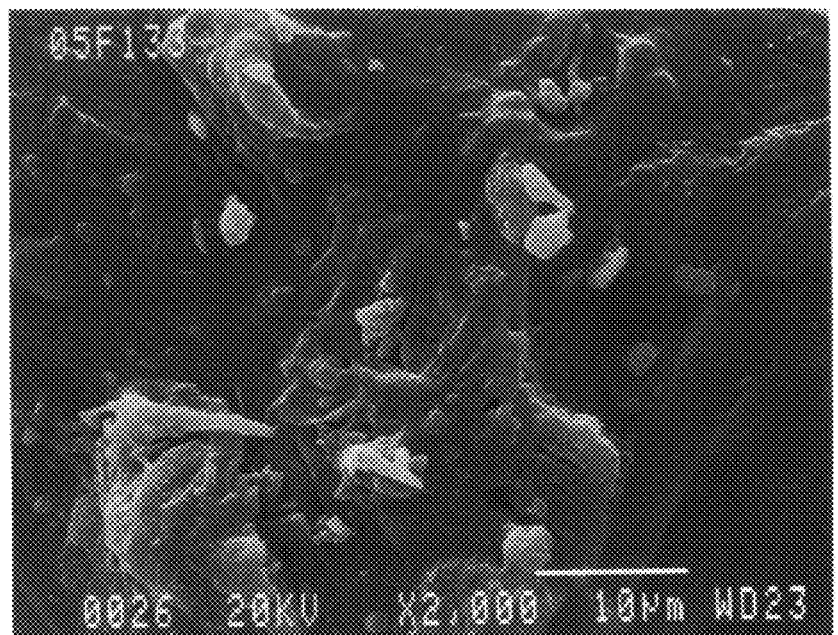
Figure 6J:
Figure 6K:
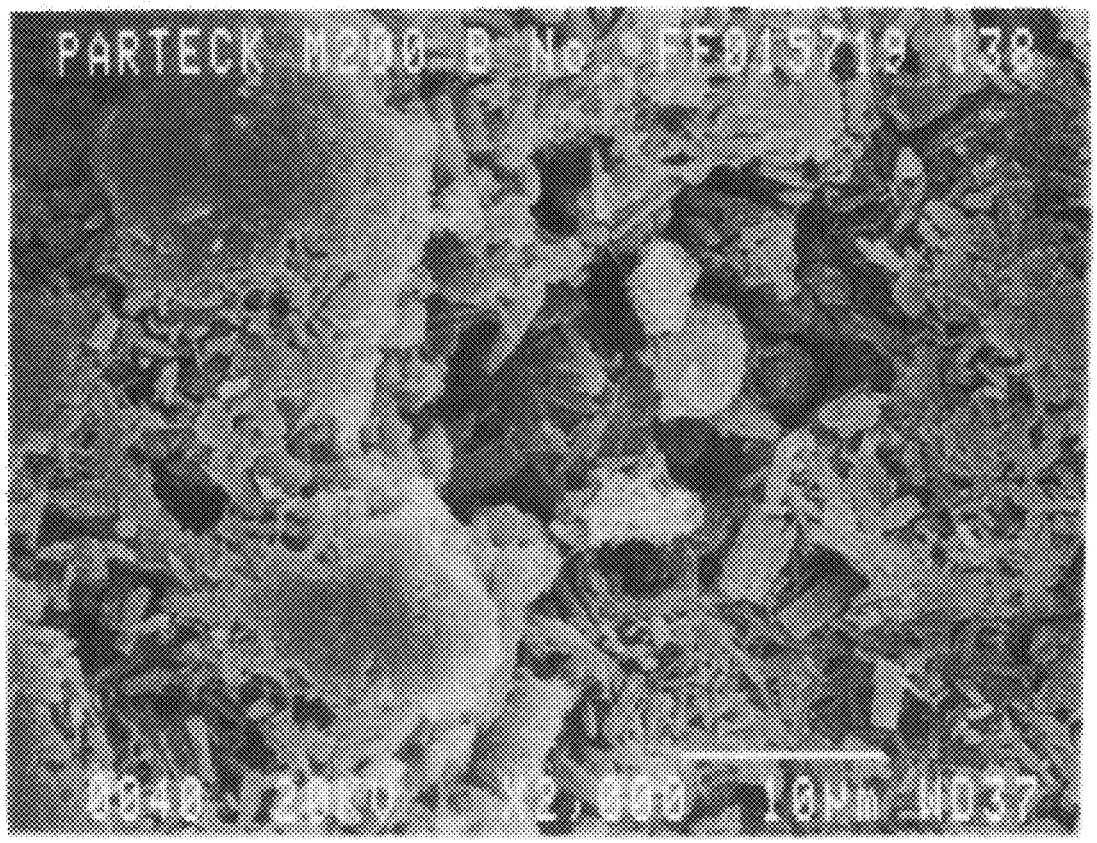
Figure 7A:
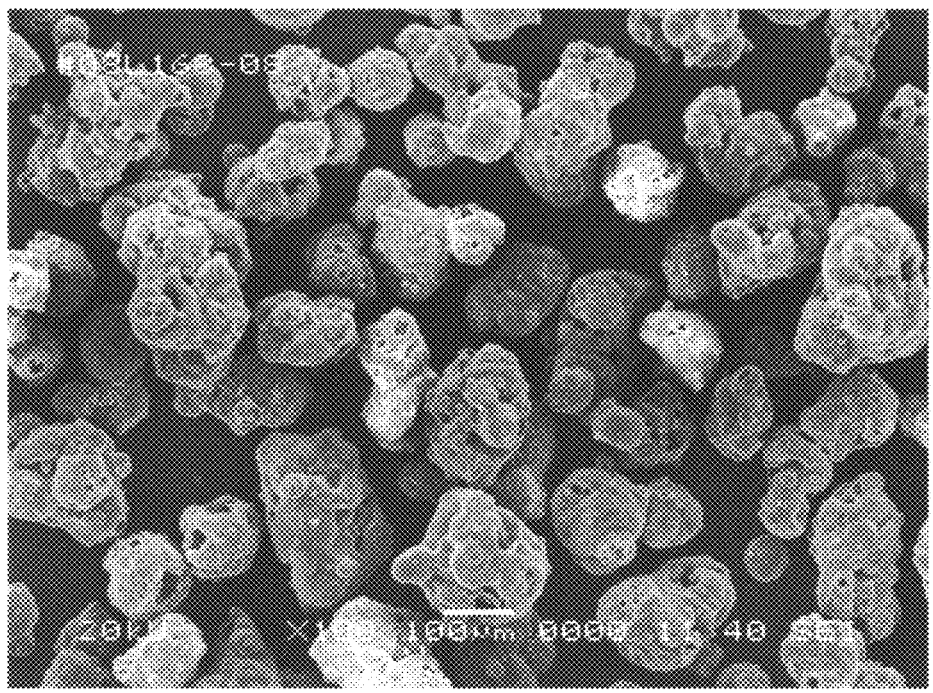
FIGS. 7A-7C, is a set of SEMs of Solid Dispersion A after co-spray drying.
Figure 7B:
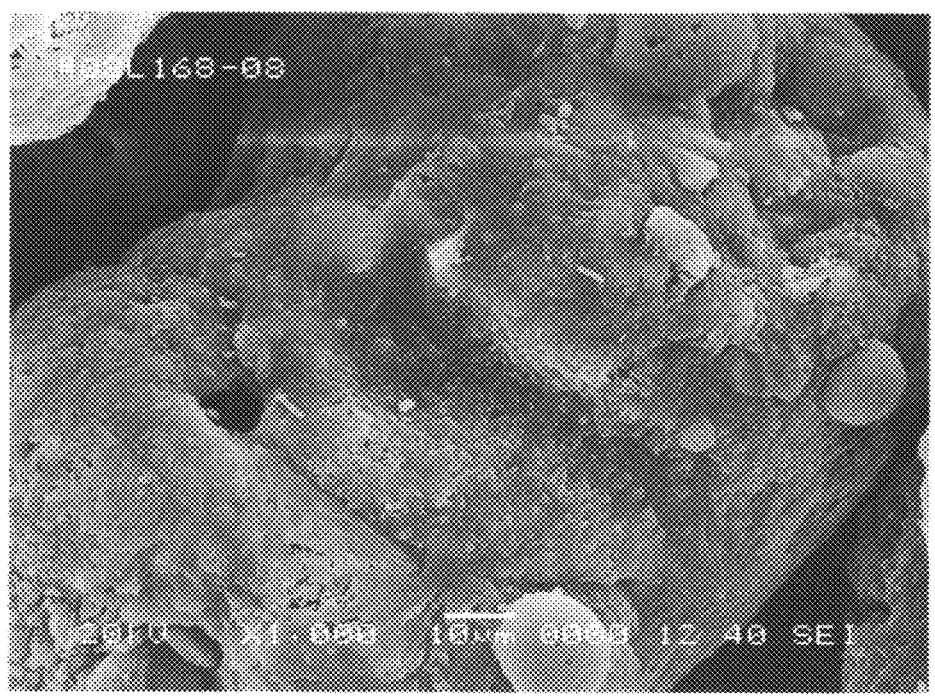
Figure 7C:
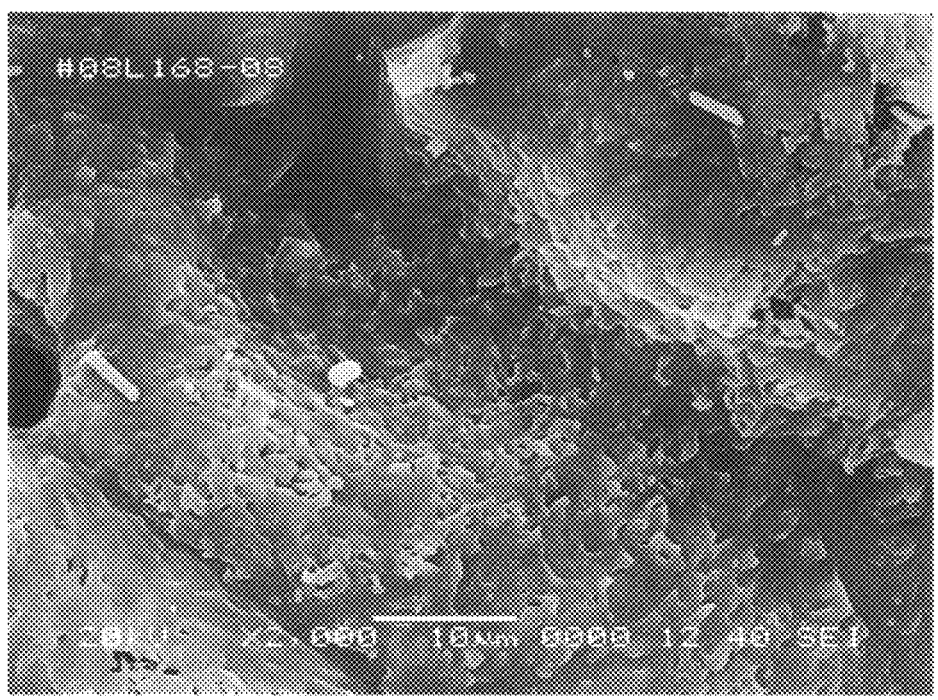

| Product | Components | FIGS. |
|---|---|---|
| 1) Mannogem ® EZ EP grade (SPI Pharma) | >98% mannitol and ~1% sorbitol | FIGS. 6A-6C |
| 2) Mannogem ® EZ USP (SPI Pharma) | >96% mannitol and ~2% sorbitol | FIGS. 6D-6F |
| 3) Mannitol HS (SPI Pharma) | >86% Mannitol and ~12% sorbitol | FIGS. 6G-6I |
| 4) Parteck ® M 200 EP grade (EM Merck, Germany) | >98% mannitol and <2% sorbitol | FIGS. 6J-6K |

Figure 8:
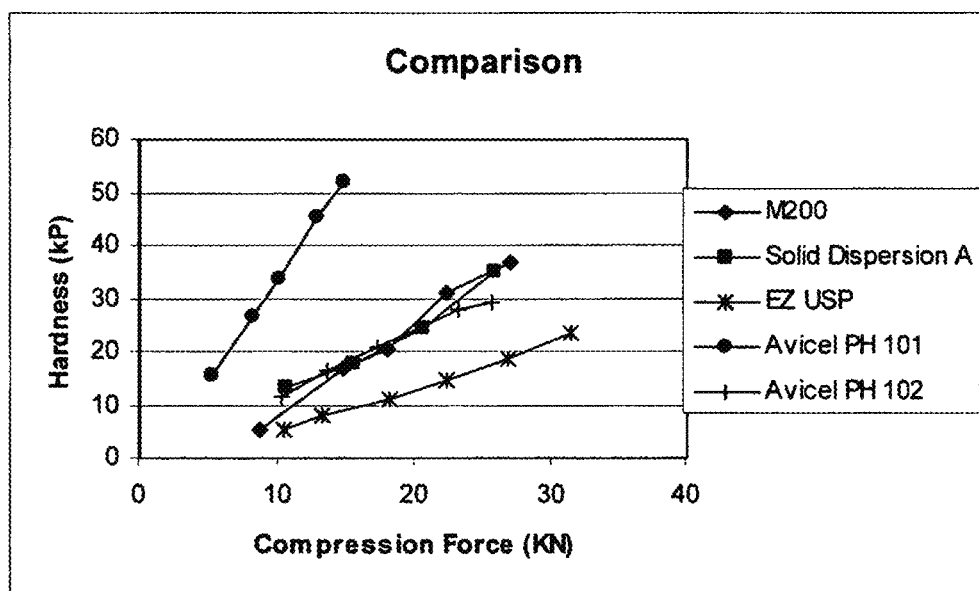
FIG. 8 is a graph depicting hardness as a function of compression force for comparison of tableted Solid Dispersion A to other excipients.
Figure 9:
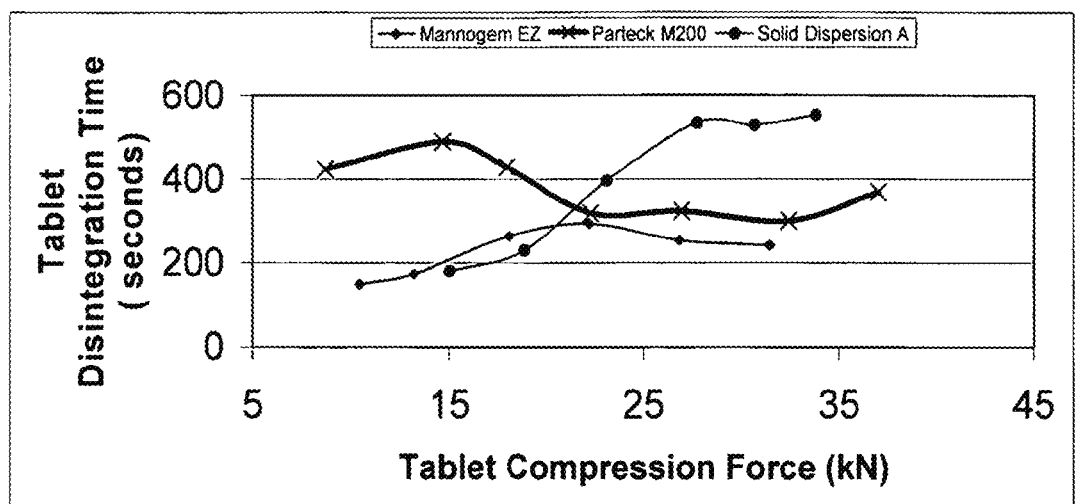
FIG. 9 is a graph depicting disintegration as a function of compression force for comparison of tableted Solid Dispersion A to other excipients.

FIGS. 6A-6C show various magnifications of Mannogem® EZ-EP grade. FIGS. 6D-6F show various magnifications of Mannogem EZ USP grade. FIGS. 6G-6I show vari- In FIG. 8, hardness is depicted as a function of compression force for comparison of tableted Solid Dispersion A to Mannogem EZ and Parteck® M200. The filamentous structure of Parteck® M200 adds to its compactability and its slope to be equivalent to Solid Dispersion A at ~1.3 kP/kN pressure. However in FIG. 9, it is demonstrated that Parteck® M200 has a longer disintegration time than Solid Dispersion A at lower pressure of force. It is thought that Solid Dispersion A is moving at low pressure due to its microcrystalline plate structure versus Parteck® M200's structure that at similar low pressures is spreading the filamentous deposit into pores and filling them.

It is evident that the improvement gained via this invention is the development of a higher hardness with lower pressure without the loss of disintegration time. Another advantage of the present invention is the ability to control the thickness of the microcrystalline plate structure. The earlier in the process the dispersed phase of the solid dispersion is co-crystallizing, the thinner the mannitol layer in the microcrystalline plate structure. The later in the co-crystallization process the thicker the mannitol layer. An additional advantage of the present invention is the low friability of the solid dosage forms. The thinner the layer in the microcrystalline plate structure, the thinner the layer the smaller the pore the deforming plate can penetrate and the more rapidly will be the stress relief in the solid dosage form matrix.

The present invention also provides the advantage of controlling the tackiness of the surface composite. The dispersant component of the solid dispersion can also be incorporated in a linear or non linear matrix design. Non linear and angled is the 1,4 linked design of lactitol and maltitol and similar 1, 4 linked polyols or disaccharides.

It is believed the glucose or galactose in the 1,4 linkage gets involved in the growth of the mannitol matrix in the most rapidly growing C dimension of the crystal pattern and segment, leaving the sorbitol portion of the disaccharide available in an angle plane to layer either mannitol, sorbitol or a glucose or galactose portion of maltitol or lactitol in a crossed crystalline arrangement. Thus mannitol wants to grow in C direction and is blocked and starts to grow in the A dimension, its slowest growing crystal face. This leads to enough growth in A dimension to form a thick enough crystal plane in the C dimension which is again blocked by attaching the glucose or galactose deposit.

A non linear model can be generated from the 1,6 linked format, which is the less angular format. Monopolyols/saccharides and disaccharadies such as 1,6 linked isomalt or similar 1,6 linked disaccharides can be used.

It is apparent the fragmented step arrangement of the non linear model is not as likely. The structure of the composite will be stiffer with less in composite area of non-crystalline transition.

Figure 10:
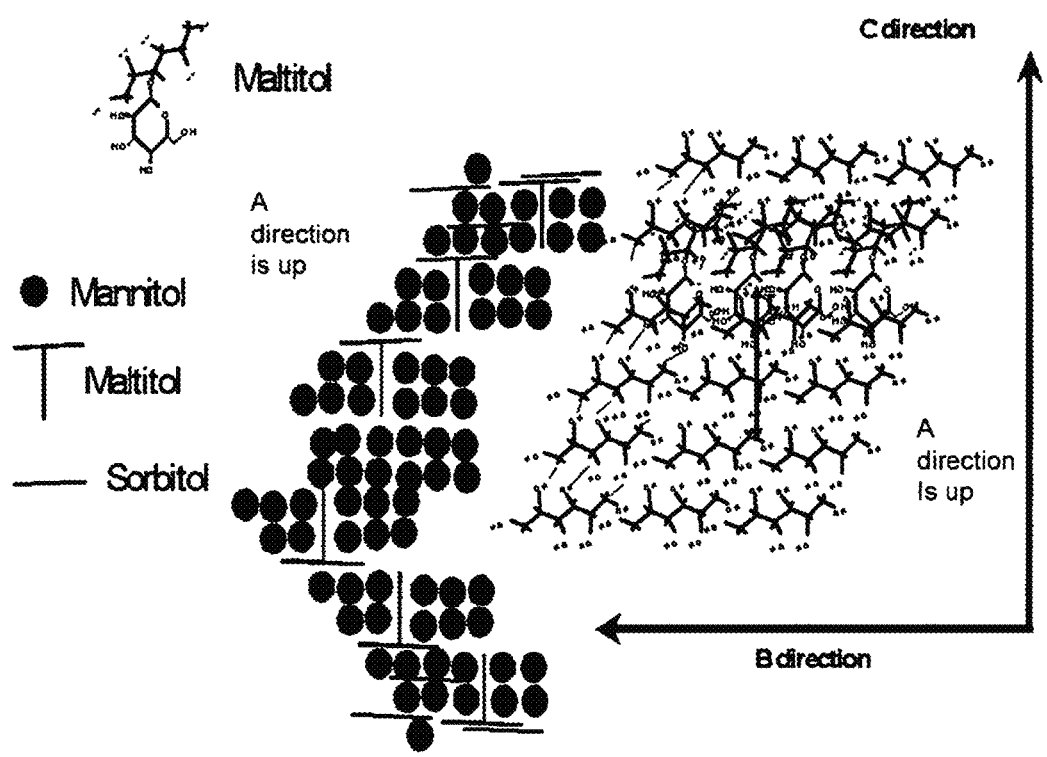
FIG. 10 is a drawing of an embodiment of the microcrystalline plate structure of the solid dispersion.

Without limiting the scope of the invention, FIG. 10 depicts a possible structural explanation for the functionality of performance of solid dispersion Solid Dispersion A. The structure of the microcrystalline plate structure consists of a core, a single or multiple stepped transition layer and a surface layer. The core is a mannitol crystal which is a naturally thin crystal structure of the Alpha and Beta crystal form. Mannitol in either Alpha or Beta form is shaped like a feather, long in the C direction, not very wide in the B direction and thin in the A direction. The transition layer above the mannitol core is segmented. The segments are in the stepped configuration are due to the glucose ring of in this example maltitol which incorporated into the fastest growing C direction plate. Angled off this glucose portion inclusion and oriented in the A growth surface is the sorbitol portion of the maltitol. The sorbitol portion of maltitol insertion in the A direction attracts mannitol to it in the transition layer. As sorbitol in maltitol is linked in the sorbitol 4 position the sorbitol attraction is maximized to take advantage of sorbitol high dielectric constant of 35.5 (Handbook of Chemistry and Physics, $84^{th}$, D. Lide CRC press). The draw of mannitol firms up the film in the C direction plasticize it and yet allows the glucose portion to segment the transition layer for tablet pressure deformation. In the surface layer sorbitol is now also co-crystallizing with the maltitol and mannitol. The sorbitol adds in with its higher polar side down on the maltitol sorbitol inclusion in the A surface direction. This given a lower surface polar bond tacking energy from the weaker polar side now up to the A surface allowing lower pressure dissociation of the microplate during tableting.

Example 3

Microcrystalline Plate Structure Bond Strength

In one embodiment, a particle of the solid dispersion consists of microcrystalline plates. The microcrystalline plates have three distinct zones, the core, a transition zone and a surface zone. To make a particle these micorplates are stacked in layers one on another like a "onion". The particles in some embodiments are hollow. Thus the "onion" layer of microplates is on the exterior surface like on a bubble, with the "onion" layered microplates being the layers in the skin.

Two factors in tabletting are used to form bonds and make a tablet harder as a greater compression force is applied. One factor is more surface coming in close contact (loss in porosity) and bonding and the second is the bond strength per unit surface of the formulation. Two special conditions are needed for hardness of tablets. The bond strength per surface area needs to be high, and the area of contact per total surface area present in material should be high.

The bond strength between the microplates is controlled by the surface composition of the microplate. At low pressure the interphase between microplate surfaces becomes a fracture line generating microplate splinters as can be seen in the FIG. 3 of Solid Dispersion A tablet cross section SEM. The reason for the splintering is the weakened microplate interphase bond, the microplate thinness and the continuous, yet fragmented structural nature of the microplate.

From a functional view the lack of change in friability and the durability of the tablet surface or skin are also evidence of the bonding weakness of the microplate. As the porosity of the tablet is closing from 13 kN force applied to 33 kN force the low friability and high durability of the tablet surface is developed and remains unchanged even at the higher forces applied.

To calculate porosity in the tablet, the density of the tablet is compared in a ratio of the true density of the tableting materials. Solid Dispersion A true density was measure using a Quantachrome (Palm Beach, Fla.) helium pycnometry at 1.435 gm/ml. Tablet density is found by using tablet weight and dividing by tablet volume. Tablet volume is tablet thickness and the tablet diameter 15.87 mm (0.625 inches) to calculate the volume of a cylinder. % Porosity is the 1−(tablet density)/(1.435 gm/ml)*100.

An estimate of bonding strength per unit area can be obtained by calculating the radial tensile strength at zero porosity, a point where all surfaces are theoretically touching.

Figure 11:
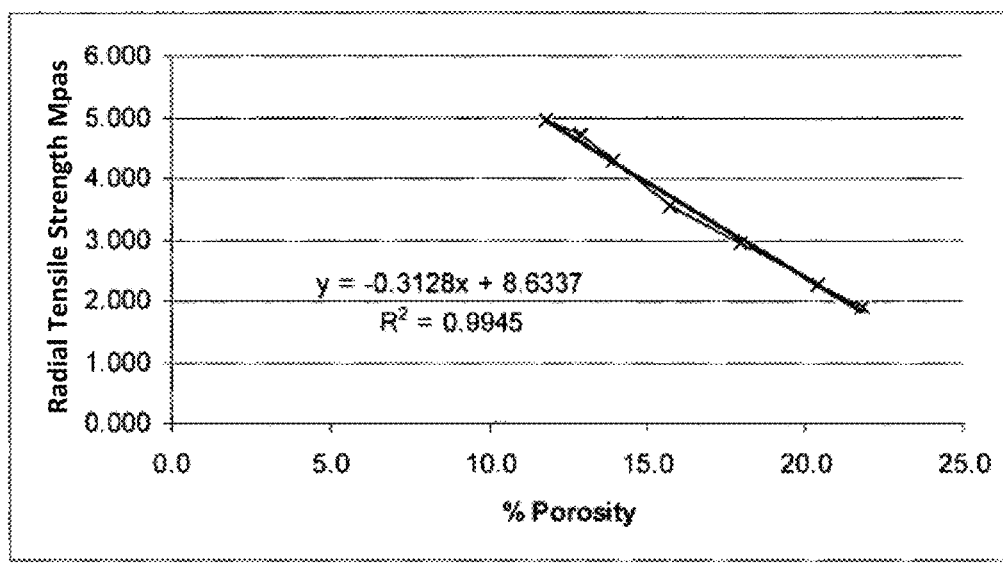
FIG. 11 is a graph depicting radial tensile strength as a function of % porosity for tableted Solid Dispersion A.
Figure 12:
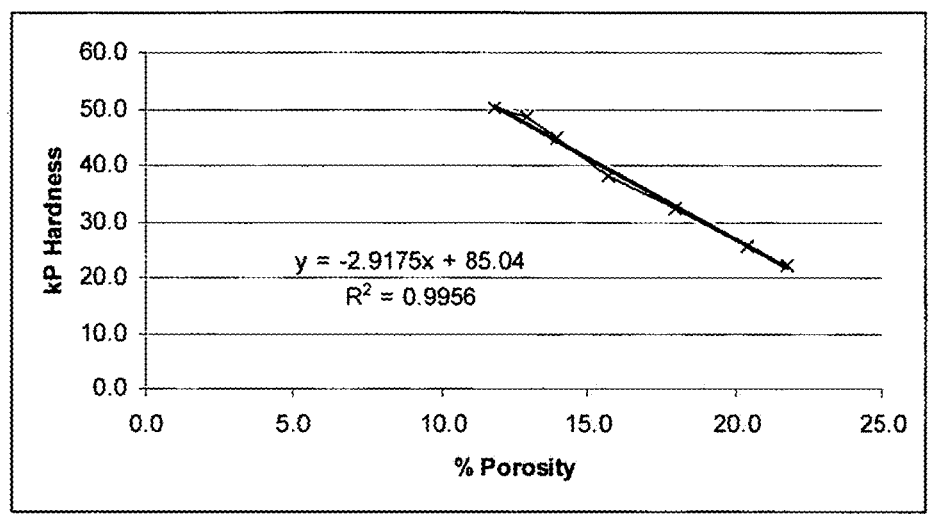
FIG. 12 is a graph depicting hardness as a function of % porosity for tableted Solid Dispersion A.

Radial tensile strength (RTS) was calculated for the tablet (see USP 32, Chapter 1217 for test and calculation method). FIG. 11 depicts the RTS as a function of porosity. The RTS strength at zero porosity of 8.6 Mpa as seen in FIG. 11 is substantial, producing a tablet with a breaking force of 85 kP. See FIG. 12 for plot of % porosity versus breaking force. Most one gram tablets as chewable as 0.625 inch diameter FFBE would be considered too hard at 20 kP breaking force.

Figure 13:
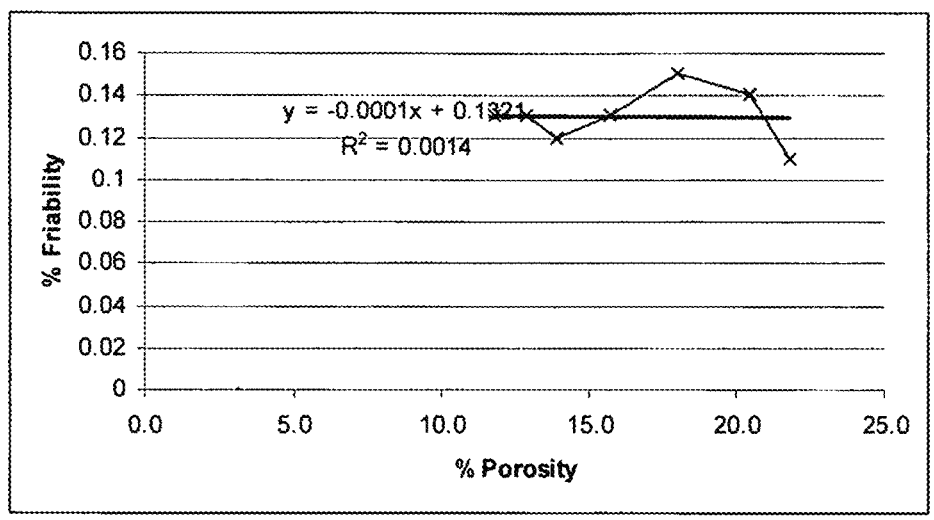
FIG. 13 is a graph depicting % friability as a function of % porosity for tableted Solid Dispersion A.

In FIG. 13 for the same tablet run featuring % porosity versus very high hardness from 13 kN to 35 kN compression force it is very obvious that a very low friability of <0.16% is achieved at 13 kN force and is maintained at pressure up to 33 kN force range ($R^2$=0.0014). To achieve such low friability at such a low pressure the bond strength between plates in the surface zone of the microplate must be low to allow fracture, yet to achieve such a high bond per unit area of 85 kp the bond formation in the transition zone deformation must be high. We believe this is accomplished in four ways. 1) Microplates surface zone has low bond energy allowing the plates to fracture at low pressure (FIG. 3 of Solid Dispersion A tablet cross section shows fractured plates). 2) The plates are very thin and thus can move into small spaces in tablet that are open. 3) The transition zone is deformable under pressure to give a high bond per unit area. 4) The core of the microcrystal is a very durable crystal that forms the hardness of the tablet in combination to 3 developing the deformation and total surface to surface bond at 85 kP.

In this embodiment of the present invention the breaking force is 85 KP, which is an exceptionally hardened tablet at zero porosity. Most amazing is the linear response to strength increase with force applied, which generally, means the only factor changing is the increase in tablet strength through bond formation. With bond strength per surface area fixed at 8.6 Mpas, the factor changing in a linear fashion is the loss in porosity and a greater amount of surface coming in close contact and bonding. This very high bonding energy per unit surface allows higher tablet strength with less surface contact area. Thus dilutability by adding actives and other needed ingredients still allows for production of acceptable tablets both in durability and hardness.

Example 4

Uniformity of Densification

Solid Dispersion A, as described in Example 1, is formulated and compared with Fast Flo® Lactose (Wisconsin Dairies, Appleton, Wis.) in a 500 mg acetaminophen tablet formulation in an 850 mg tablet. The formulations have Compap L a direct compression grade of acetaminophen by Covidien (St. Louis, Mo.) at 65.65%, Copovidone S-630 (ISP, Wayne, N.J.) at 3%, Crosspovidone XL-100 (ISP, Wayne, N.J.) at 2% and Magnesium Stearate of Covidien (St. Louis, Mo.) at 1.5%. Tablets were made on a Minipress II made by Globe Pharma (New Brunswick, N.J.) using 0.3125×0.72 caplet shaped tooling at 21 RPM.

Figure 14:
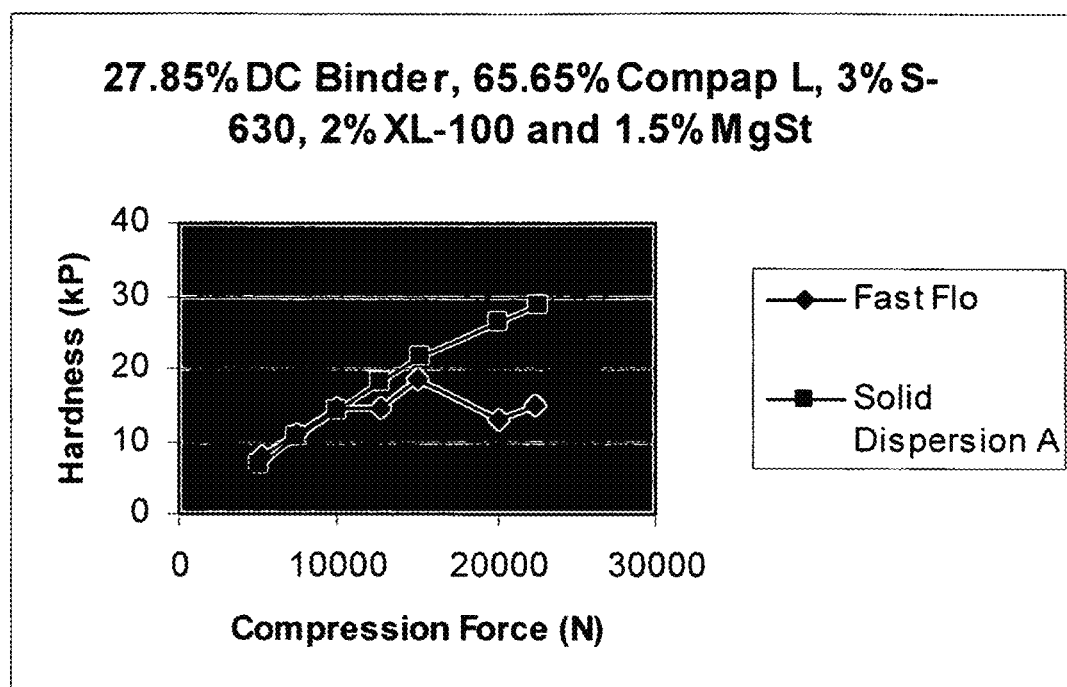
FIG. 14 is a graph depicting hardness as a function of compression force for comparison of tableted Solid Dispersion A and Fast Flo® lactose (Wisconsin Dairies) formulations.

In FIG. 14, the 27.85% of Solid Dispersion A added to the mixture shows a linear rise in hardness of tablet with increasing compression force. Note at the same level, 27.85% of Fast Flo® lactose the hardness of the tablets is linear only up to 10 kN of force. Above 10 kN of force the linearity is lost and hardness does not increase.

Figure 15:
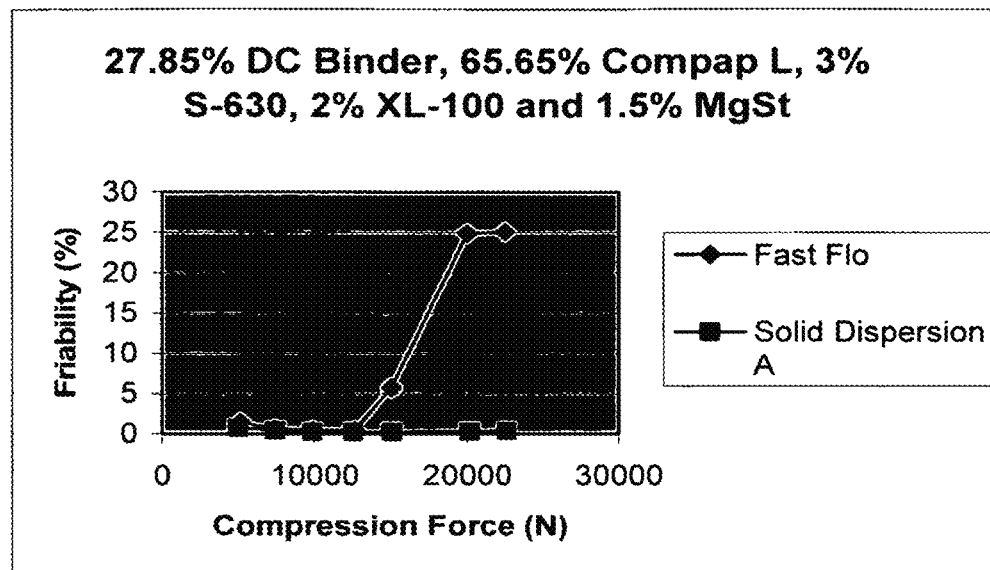
FIG. 15 is a graph depicting friability as a function of compression force for comparison of tableted Solid Dispersion A and Fast Flo® lactose (Wisconsin Dairies) formulations.

In FIG. 15, the friability of the Solid Dispersion A formulation is compared with FastFlo® lactose formulation. The friability of Solid Dispersion A is well below 1% in the formulation and stays below 1% for the entire compression force profile for Solid Dispersion A. This is not the case for Fast Flo® lactose which at 12 kN the friability of the tablet is increasing, giving evidence to the failing durability of the tablet structure. This durability failure results from a build up of internal stress with the higher compaction pressures and the resultant elastic recovery of the structure. Solid Dispersion A under pressure is flowing into unoccupied spaces in the tablet matrix relieving the pressure build up. Solid Dispersion A based upon the linearity of hardness with pressure and maintenance of durability in the friability test with pressure build up demonstrates the ability of Solid Dispersion A to flow from areas of higher pressure to areas of lower pressure in a linear manner.

Note the flat line for friability does not increase with compression force. Lactose shows low friability at lower pressure, but due to pressure build up in the structure the tablet ruptures at higher pressure. Additionally, the hardness of Solid Dispersion A climbs linearly with compression force. The Fast Flo® lactose does not climb in hardness after an increase in pressure due to the build up of density/pressure centers without forming more bond strength. The Solid Dispersion A plates are still moving into open smaller spaces at higher pressure and creating bonding surfaces where pores were once present/open.

Example 5

Fast Disintegrating Excipient System and Pharmaceutical Formulation

| Excipient System A | | |
|---|---|---|
| Ingredient # | Ingredient Name | Wt % |
| 1 | Solid Dispersion A | 49 |
| 2 | Mannogem EZ | 15 |
| 3 | Silicon Dioxide | 1 |
| 4 | Mannogem EZ (about 99 wt %) coated with soluble polymer material (about 1 wt %) | 20 |
| 5 | Crospovidone XL | 15 |

| Formulation A | | |
|---|---|---|
| Ingredient # | Ingredient | Wt % |
| 1 | Taste-masked acetaminophen (93%) | 38.4 |
| 2 | Excipient System A (as described above) | 45.9 |
| 3 | Natural peppermint flavor | 2 |
| 4 | Sucralose | 1.25 |
| 5 | Silicon dioxide | 1 |
| 6 | Plasdone ® S-630, copovidone | 3 |
| 7 | Plasdone ® XL, crospovidone | 5.9 |
| 8 | Blue lake 5516 | 0.05 |
| 9 | Sodium stearyl fumarate | 2.5 |

In order to make a 60 kg batch of Excipient System A, 29.4 kg of previously co-processed mannitol (about 96%), maltitol (about 1.7%), and sorbitol (about 2.3%) (SPI Pharma; Wilmington, Del.), 2.) 9.0 kg of Mannogem EZ (SPI Pharma; Wilmington, Del.), 3.) 0.6 kg of Syloid 244FP EU (Grace Davison; Colombia, Md.), 4.) 12.0 kg of EZS1 (SPI Pharma; Wilmington, Del.), 5.) 9.0 kg of crospovidone XL (Nanhang; Hangzhou, China) were weighed out using an electronic scale. The mannitol, maltitol, sorbitol, Mannogem EZ, EZS1 and crospovidone XL were screened through a 48" or 60" Sweco screening apparatus (Sweco; Florence, Ky.) assembled with a #30 stainless steel square hole mesh (Sweco; Florence, Ky.). Syloid 244FP EU was passed through a #20 stainless steel hand screen with square hole mesh (Custom Advanced; Webster, Tex.). After screening, all components were collected. The screened materials were charged by hand into a 10 cubic foot V-blender (Patterson-Kelly; East Stroudsburg, Pa.) in the following order: 15.0 kg of co-processed mannitol, maltitol and sorbitol, 0.6 kg of Syloid 244FP EU, 14.4 kg of co-processed mannitol, maltitol, sorbitol, 9.0 kg of Mannogem EZ, 9.0 kg crospovidone XL, and 12.0 kg of EZS1. The materials were blended in V-blender set at 25 rpm for a total of 15 minutes. The blend was discharged from the bottom port of V-blender into a double polylined drum. 2.5% of sodium stearyl fumarate was blended in prior to tableting.

In order to make 1 kg of Formulation A which is subsequently compressed into a 500 mg APAP orally disintegrating tablet (ODT) with a total weight of 1400 mg, 384 g of taste-masked Acetaminophen (Eurand; Yardley, Pa.), 2.) 459 g of Excipient A (SPI Pharma; Wilmington, Del.), 3.) 20 g of Natural Peppermint flavor (Givaudan; Cincinnati, Ohio), 4.)

12.5 g of Sucralose (Tate & Lyle; London, England), 5.) 10 g of silicon dioxide (Grace Davison; Colombia, Md.), 6.) 30 g Plasdone S-630 (ISP; Wayne, N.J.), 7.) 59 g of Crospovidone XL (Nanhang; Hangzhou, China), 8.) 0.5 g Blue lake 5516 (Colorcon; Harleysville, Pa.), 9.) and 25 g sodium stearyl fumarate (SPI Pharma; Wilmington, Del.) were weighed out using an electronic scale. Subsequent to weighing, ingredients 1, 2, 3, 4, 5, 6, and 7 were screened through a #20 stainless steel screen with square-hole mesh (Custom Advanced; Webster, Tex.). Ingredients 8 and 9 were co-screened through a #20 stainless steel screen with square-hole mesh (Custom Advanced; Webster, Tex.). After screening, all ingredients, except ingredients 8 and 9 (already co-screened) by hand, were placed into an 8-quart V-blender (Patterson-Kelley; East Stroudsburg, Pa.), in the following order: total of 1, total of 2, total of 3, total of 4, total of 5, total of 6 and total of 7. Materials were blended in V-blender set at 25 rpm for a total of 15 minutes. To the resultant blend, the co-screen of ingredients 8 and 9 were added and blended for an additional 5 minutes in the 8-quart V-blender at 25 rpm. The blend was discharged from the bottom port of the V-mixer into a polyline bag. The collected blend was placed into the hopper of a GP-8 rotary tablet press (Globe Pharma; New Brunswick, N.J.) outfitted with one station of 0.625" FFBE "D" tool upper punch, lower punch, and die (Natoli Engineering; St. Charles, Mo.). The blend was tableted into 1400 mg weight tablets at 25 rpm with 2 kN of pre-compression, adjusting the main compression to obtain a tablet hardness of 6 to 7 kP.

Figure 16:
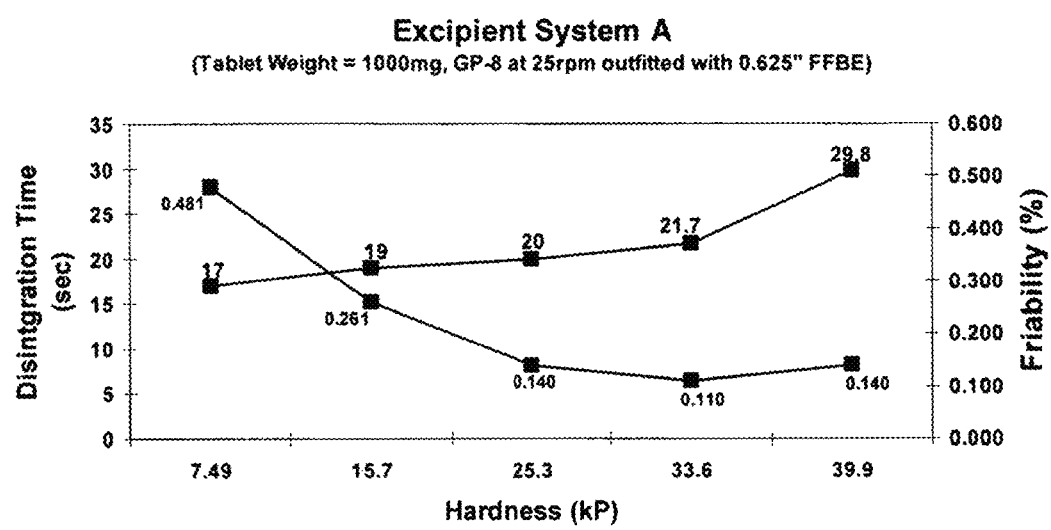
FIG. 16 is a graph depicting disintegration and friability as a function of hardness for tabletted Excipient System A.

A relationship between disintegration and friability as a function of hardness for tabletted Excipient System A is shown in FIG. 16.

As illustrated in FIG. 16, an excipient system of some embodiments of the present invention exhibits a lower dependence of disintegration time and friability on hardness. In some embodiments, an excipient system of the present invention may disintegrate rapidly at high hardness values. In some embodiments, an excipient system of the present invention rapidly develops a creamy mouth feel upon disintegration. As illustrated in FIG. 16, an excipient system of the present invention may unexpectedly disintegrate in less than about 30 seconds at a hardness value of about 39.9 kP, and in some embodiments can rapidly develop a creamy mouth feel upon disintegration. In some embodiments, an excipient system exhibits desirable disintegration times and friability values at a wide range of hardness values. In some embodiments, an excipient system exhibits a low increase in disintegration time per increase in hardness values.

Example 6

Fast Disintegrating Excipient System B and Pharmaceutical Formulations

Coating Solution B

| Ing. # | ITEM | (MFG, Location) | Percent | QTY (Kg) |
|---|---|---|---|---|
| 1 | Plasdone S-630 | (ISP, Colombia, MD) | 11.98 | 9.2 |
| 2 | Purified Water | N/A | 88.02 | 67.6 |
| | Total Wt. (Dry Basis) | | 11.98% | 9.2 |

67.6 kg of purified water was charged into a solution tank, outfitted with an agitator. While agitating the purified water, Plasdone S-630 was slowly added to the tank. Agitation was continued until a uniform dispersion of the Plasdone S-630 in purified water was achieved. Coating Solution B was used within 12 hours of obtaining the uniform dispersion. The solution was kept under continuous agitation during subsequent processing steps.

Coated Solid Dispersion A

| Ing. # | ITEM | (MFG, Location) | Percent | QTY (Kg) |
|---|---|---|---|---|
| 1 | Solid Dispersion A | (SPI, Wilmington, DE) | 92.29 | 400 |
| 2 | Coating Solution B | (SPI, Wilmington, DE) | 7.71 | 33.4 |
| | Total Wt. (Dry Basis) | | 93.22% (Dry weight of 404 kg/ 433.4 kg) | 404 |

400 kg of Solid Dispersion A was weighed out and screened using a 48 or 60" Sweco equipped with a #16 stainless steel screen with square holes. The screened Solid Dispersion A was charged into the fluid air bowl of a Fluid Air 1000. Spray nozzles were 0.066"-0.068" bore set at extended from the cap. The liquid nozzle manifold was set up with the standard extension (10.5"). The Fluid Air 1000 was operated in the following manner: airflow of 1500-3000 SCFM (target of 2000 SCFM), inlet temperature of 75° C.-100° C. (target 90° C.), solution spray rate of 0.5-2.0 kg/min (target 1.1 kg/min), atomization air pressure at 50 PSIG, approximate spraying time was 17-66 minutes. The product temperature was allowed to reach at least 30° C. prior to spraying solution. 33.4 kg of solution was sprayed on in approximately 17-66 minutes (target 30 minutes at 1.1 kg/min). The filters were manually purged for at least 5 minutes, if necessary, to maintain the minimum air flow. The granulation was dried to a product temperature of 35° C.-50° C. (target of 45° C.). When the product temperature reached approximately 45° C., a sample (2.0 g-3.0 g) was tested for moisture content. Park was pressed on the fluid bed and the filters manually purged while testing the moisture. Continued to dry and sample at approximately 10 minute intervals until target moisture (target of <1.0%) was reached. When the moisture was <1.0%, the fluid bed was shutdown and the product cooled to 35° C. The filters were manually purged for at least 5 minutes. The resulting product, Solid Dispersion B, was sifted through a 48" or 60" Sweco equipped with a #16 stainless steel screen with square holes. The product was packaged in double poly-lined drums.

| Excipient System B | | | | |
|---|---|---|---|---|
| Ing. # | ITEM | (MFG, Location) | Percent | QTY (Kg) |
| 1 | Solid Dispersion A | (SPI Pharma, Wilmington, DE) | 64.54 | 68.4 kg |
| 2 | Crospovidone XL | (Nanhang Ind. Co., Hangzhou, China) | 15.13 | 16.0 kg |
| 3 | Coated Solid Dispersion A | (SPI Pharma, Wilmington, DE) | 20.17 | 21.4 kg |
| 4 | Syloid 244 FP EU | (Grace Davison, Columbia, MD) | 0.16 | 0.2 kg |
| | Total Wt. (Dry Basis) | | 100 | 106 kg |

The above listed ingredients were weighed in the amounts indicated on an electronic balance. Subsequent to weighing, ingredients 1, 2, and 3 were screened through a previously assembled 48" or 60" Sweco screening apparatus (Sweco; Florence, Ky.) assembled with a #20 stainless steel (Sweco; Florence, Ky.) square-hole mesh. Subsequent to weighing, ingredient 4 was passed through a #20 stainless steel hand screen with square-hole mesh (Custom Advanced; Webster, Tex.). After screening, all components were collected in separate, labeled 37×80×0.0035 Natural Co-ex polyethylene bags. The weighed and screened ingredients were charged by hand into a 10 cubic foot V-blender (Patterson-Kelly; East Stroudsburg, Pa.) in the following order: 1) 34.2 kg of Solid Dispersion A, 2) 0.16 kg of Syloid 244 FP EU, 3) 20.17 kg of Solid Dispersion B, 4) 15.13 kg of Crospovidone XL, and 5) 34.2 kg of Solid Dispersion A. Materials were blended in V-blender set at 25 rpm for a total of 15 minutes. Blend was discharged from bottom port of V-blender into a double polylined drum.

| 160 mg Acetaminophen (APAP) Orally Disintegrating Tablet | |
|---|---|
| Taste-masked Acetaminophen (93.4% APAP) | 28.55% |
| Excipient System B | 66.20% |
| Sucralose | 1.25% |
| Bubblegum Flavor | 2.00% |
| Sodium stearyl fumarate | 2.00% |

For a batch size of 1000 g, the above ingredients were weighed and separately screened through a #20 stainless steel square hole mesh. Each ingredient, except the sodium stearyl fumarate, was placed in an 8-quart V-blender and mixed for 15 minutes at a speed of 25 rpm. After 15 minutes, the sodium stearyl fumarate was added to the blend and mixed for 5 additional minutes at a speed of 25 rpm. The resultant blend was emptied from the bottom discharge port of the blender into an appropriate plastic bag. The blend was placed in the hopper of a GP-8 instrumented tablet press outfitted with 0.5"×0.5" arc square punch "D" tool set (upper punch, lower punch, and die) with a cup depth of 0.0730" (Hob#104152, Natoli Engineering, St. Charles, Mo.) and compressed into 600 mg tablets at a rotary speed of 36.7 rpm with a pre-compression force of 1 kN and to a tablet hardness of 5-7 kP as determined by a Model 6D Dr. Schleuniger tablet hardness tester.

| 500 mg Acetaminophen (APAP) Orally Disintegrating Tablet | |
|---|---|
| Taste-masked Acetaminophen (93.4% APAP) | 38.40% |
| Excipient System B | 44.40% |
| Peppermint Flavor | 2.00% |
| Sucralose | 1.50% |
| Sodium stearyl fumarate | 2.50% |
| Crospovidone XL | 4.20% |
| Microcrystalline Cellulose-101 | 7.00% |

For a batch size of 500 g, the above ingredients were weighed and separately screened through a #20 stainless steel square hole mesh. Each ingredient was placed in an 8-quart V-blender and mix for 15 minutes at a speed of 25 rpm, except for the sodium stearyl fumarate. After 15 minutes, the sodium stearyl fumarate was added to the blend, and blend mixed for 5 additional minutes at a speed of 25 rpm. The resultant blend was emptied from the bottom discharge port of the blender into an appropriate plastic bag. The blend was placed in the hopper of a GP-8 instrumented tablet press outfitted with a 0.66"×0.66" Arc Square "D" tool set (upper punch, lower punch, and die) with a cup depth of 0.0320" (Hob #105192, Natoli Engineering, St. Charles, Mo.) and compressed into 1400 mg tablets at a rotary speed of 25 rpm with a pre-compression force of 2 kN and to a tablet hardness of 5-7 kP as determined by a Model 6D Dr. Schleuniger tablet hardness tester.

| 10 mg Loratidine Orally Disintegrating Tablet | |
|---|---|
| Loratidine | 10.00% |
| Excipient System B | 84.50% |
| Bubblegum flavor | 2.00% |
| Sucralose | 1.00% |
| Sodium Stearly Fumarate | 2.50% |

For a batch size of 500 g, the above ingredients were weighed, and separately screened through a #20 stainless steel square hole mesh. Each ingredient, except the sodium stearyl fumarate, was placed in an 8-quart V-blender and mixed for 15 minutes at a speed of 25 rpm. After 15 minutes, the sodium stearyl fumarate was added to the blend, and mixed for 5 additional minutes at a speed of 25 rpm. The resultant blend was emptied from the bottom discharge port of the blender into an appropriate plastic bag. The blend was placed in the hopper of a GP-8 instrumented tablet press outfitted with a 0.25" FFBE set (upper punch, lower punch, and die) and compressed into 100 mg tablets at a rotary speed of 25 rpm and to a tablet hardness of 1-3 kP as determined by a Model 6D Dr. Schleuniger tablet hardness tester.

Example 7

Manufacturing of 500 mg Acetaminophen Caplet-Shaped Swallow Tablets with Solid Dispersion A For a 2.0 kg batch of a 500 mg acetaminophen tablet with Solid Dispersion A, the following ingredients were weighed out: 1) 557 g of Solid Dispersion A (SPI Pharma; Wilmington, Del.), 2) 1313 g of Compap L (Covidien, St. Louis Mo.), 3) 60 g of Plasdone S-630 (ISP Corp, Wayne, N.J.), 4) 40 g of Crospovidone XL-100 (Nanhang, Hangzhou, China) and 5) 30 g of Magnesium Stearate (Covidient St. Louis, Mo.). Subsequent to weighing, the ingredients were screened through US #20 stainless steel (Sweco; Florence, Ky.) square hole mesh. The weighed and screened ingredients were charged into a 8 quart V-blender (Patterson-Kelly; East Stroudsburg, Pa.) in the following order: one half of 1, total of 2, second half of 1, total of 3, and total of 4. The material was blended in V-blender set at 25 rpm for a total of 15 minutes. Ingredient 5 was added and blended an additional 3 minutes. The blend was discharged from the bottom port of V-blender into a double polylined drum.

The 500 mg acetaminophen caplet tablets with a total weight of 850 mg were compressed as follows. The blend was placed into the hopper of a GP-8 rotary tablet minipress (Globe Pharma; New Brunswick, N.J.) outfitted with at least one station of 0.3125" by 0.720" keyed D tools upper punch, lower punch, and die (Natoli Engineering; St. Charles, Mo.). The blend was tableted into 850 mg weight tablets at 25 rpm with up to 2 kN of pre-compression, adjusting the main compression to obtain a tablet hardness of 6 to 28 kP as desired.

Above 7.5 kN compression pressure, the friability is less than 0.5% and at maximum pressure of 22 kN the hardness is 28 kP and friability is <0.4%.

Example 8

1000 mcg B12 Lozenge Formulation with Solid Dispersion A

| Ing. # | Component | % | g/blend |
|---|---|---|---|
| 1 | Vitamin B12 (1% in mannitol) | 21.51 | 107.53 |
| 2 | Solid Dispersion A | 54.59 | 272.97 |
| 3 | Sorbitab SD 250 | 20.00 | 100.00 |
| 4 | Sucralose | 0.40 | 2.00 |
| 5 | Lubripharm | 3.00 | 15.00 |
| 6 | Grape Flavor | 0.10 | 0.50 |
| 7 | Purple Lake | 0.40 | 2.00 |
| | Total | 100 | 500 |

In order to manufacture Vitamin B12 lozenges containing 1000 mcg of Vitamin B12 in a 465 mg lozenge, the ingredients were first weighed on an electronic balance according to the table. All ingredients were passed through a #20 stainless steel mesh with square holes. All ingredients, except for ingredient #5, were blended in an 8-quart V-blender at 25 rpm for 15 minutes. Subsequent to blending, ingredient #5 was added to blend 1, and mixed for 5 minutes in the 8-quart blender at 25 rpm for 5 minutes. The resultant blend was removed through the inferior discharge port of the blender into an appropriate plastic bag. The blend was introduced into the hopper of a GP-8 instrumented tablet press outfitted with an 11.1-mm FFBE "D" tool punch set (upper, lower, and die). The blend was compressed into 465 mg weight lozenges at a rotary speed of 25 rpm and to a tablet hardness of 14-18 kP.

It will be appreciated by persons skilled in the art that numerous variations and/or modifications may be made to the invention shown in the specific embodiments without departing form the spirit and scope of the invention as broadly described. Thus, it is intended that the present invention cover the modifications and variations of the present invention provided they come within the scope of the appended claims and their equivalents.

What is claimed is:

1. A solid dosage form comprising a solid dispersion, the solid dispersion comprising a combination of at least three co-processed carbohydrates with different solubilities in water and/or concentrations in water,
wherein the solid dispersion has a microcrystalline plate structure comprising layers of crystalline and/or eutectic amorphous deposits,
wherein the at least three co-processed carbohydrates are polyols comprising a first polyol present in an amount of 70 wt % to 99.5 wt % of the solid dispersion, and wherein the first polyol is mannitol.

2. The solid dosage form of claim 1, further comprising an active ingredient.

3. The solid dosage form of claim 2, wherein the solid dosage form further comprises a lubricant, optionally a disintegrant, optionally a glidant, optionally a sweetener, optionally a flavor, optionally a color, and optionally other excipients.

4. The solid dosage form of claim 3, wherein the disintegrant is selected from the group consisting of crospovidone, alginic acid, croscarmellose sodium, guar gum, microcrystalline cellulose, polacrilin potassium, powdered cellulose, sodium alginate, and sodium starch glycolate, and combinations thereof.

5. The solid dosage form of claim 1, wherein the solid dosage form has a compactability as defined by a hardness from about 22 kP to about 50 kP when about 13 kN to about 35 kN of compression force is applied.

6. The solid dosage form of claim 1, wherein the solid dosage form has a durability as defined by a friability of about 0.5% or less when about 13 kN to about 35 kN of compression force is applied.

7. The solid dosage form of claim 1, wherein the at least three co-processed carbohydrates are coated.

8. The solid dosage form of claim 1, wherein the solid dispersion is coated.

9. The solid dosage form of claim 1, wherein the layers of the microcrystalline plate structure have a thickness of about 0.5 microns to about 5 microns.

10. The solid dosage form of claim 1, wherein the at least three co-processed carbohydrates are co-spray dried.

11. The solid dosage form of claim 1, further comprising a glidant.

12. The solid dosage form of claim 11, wherein the glidant is selected from the group consisting of colloidal silica, silica gel, precipitated silica, fumed silica, talc and combinations thereof.

13. The solid dosage form of claim 1, wherein the polyols further comprise polyols selected from the group consisting of sorbitol, maltitol, lactitol, xylitol, erythritol, isomalt, and mixtures thereof.

14. The solid dosage form of claim 2, wherein the solid dosage form has a hardness of about 1 kP to about 50 kP.

15. The solid dosage form of claim 2, wherein the solid dosage form has a friability of about 0.01% to about 5%.

16. The solid dosage form of claim 3, wherein the solid dosage form is a fast disintegrating tablet or a chewable.

17. The solid dosage form of claim 16, wherein the solid dosage form disintegrates in oral cavity in less than about 60 seconds.

18. The solid dosage form of claim 2, wherein the solid dosage form is a swallow tablet or a lozenge.

19. The solid dosage form of claim 1, wherein the polyols comprise a second polyol present in an amount of about 0.5 wt % to about 30 wt % of the solid dispersion, and a third polyol present an amount of about 0.5 wt % to about 30 wt % of the solid dispersion.

20. The solid dosage form of claim 19, wherein the second polyol is maltitol or lactitol and the third polyol is sorbitol.

* * * * *